(12) United States Patent
Fullerton et al.

(10) Patent No.: US 7,817,004 B2
(45) Date of Patent: Oct. 19, 2010

(54) CORRELATED MAGNETIC PROSTHETIC DEVICE AND METHOD FOR USING THE CORRELATED MAGNETIC PROSTHETIC DEVICE

(75) Inventors: Larry W. Fullerton, New Hope, AL (US); Mark D. Roberts, Huntsville, AL (US); Herman M. Thompson, Toney, AL (US); Herman M. Thompson, Jr., Kelso, TN (US)

(73) Assignee: Cedar Ridge Research, LLC., New Hope, AL (US)

( * ) Notice: Subject to any disclaimer, the term of this patent is extended or adjusted under 35 U.S.C. 154(b) by 0 days.

(21) Appl. No.: 12/494,064

(22) Filed: Jun. 29, 2009

(65) Prior Publication Data

US 2009/0292371 A1 Nov. 26, 2009

Related U.S. Application Data

(63) Continuation-in-part of application No. 12/476,952, filed on Jun. 2, 2009.

(51) Int. Cl.
- *A61F 2/02* (2006.01)
- *A61F 2/66* (2006.01)
- *A61F 2/74* (2006.01)
- *H01F 7/20* (2006.01)
- *H01F 7/02* (2006.01)

(52) U.S. Cl. .................. 335/306; 335/285; 623/17.17; 623/27; 623/57

(58) Field of Classification Search ............... 335/285, 335/302–306; 24/303; 623/27–65
See application file for complete search history.

(56) References Cited

U.S. PATENT DOCUMENTS

| 381,968 A | 5/1888 | Tesla |
| 493,858 A | 3/1893 | Edison |
| 996,933 A | 7/1911 | Lindquist |
| 1,236,234 A | 8/1917 | Troje |
| 2,389,298 A | 11/1945 | Ellis |
| 2,570,625 A | 10/1951 | Zimmerman et al. |
| 2,722,617 A | 11/1955 | Cluwen et al. |

(Continued)

FOREIGN PATENT DOCUMENTS

FR 823395 1/1938

(Continued)

OTHER PUBLICATIONS

"BNS Series-Compatible Series AES Safety Controllers" pp. 1-17, http://www.schmersalusa.com/safety_controllers/drawings/aes.pdf (downloaded on or before Jan. 23, 2009).

(Continued)

*Primary Examiner*—Ramon M Barrera
(74) *Attorney, Agent, or Firm*—William J. Tucker

(57) ABSTRACT

A prosthetic device is described herein that incorporates correlated magnets which enable an artificial prosthesis (e.g., artificial limb) to be easily and effectively attached to and removed from an interface that is secured to a residual limb on a person. In addition, a method is described herein for enabling a person to attach and remove an artificial prosthesis to and from an interface that is secured to a residual limb on the person.

21 Claims, 16 Drawing Sheets

U.S. PATENT DOCUMENTS

| | | | |
|---|---|---|---|
| 2,932,545 | A | 4/1960 | Foley |
| 3,102,314 | A | 9/1963 | Alderfer |
| 3,208,296 | A | 9/1965 | Baermann |
| 3,288,511 | A | 11/1966 | Tavano |
| 3,468,576 | A | 9/1969 | Beyer et al. |
| 3,474,366 | A | 10/1969 | Barney |
| 3,802,034 | A | 4/1974 | Bookless |
| 4,079,558 | A | 3/1978 | Gorham |
| 4,222,489 | A | 9/1980 | Hutter |
| 4,453,294 | A | 6/1984 | Morita |
| 4,536,898 | A * | 8/1985 | Palfray ................. 623/33 |
| 4,547,756 | A | 10/1985 | Miller et al. |
| 4,629,131 | A | 12/1986 | Podell |
| 4,941,236 | A | 7/1990 | Sherman |
| 5,050,276 | A | 9/1991 | Pemberton |
| 5,367,891 | A | 11/1994 | Furuyama |
| 5,383,049 | A | 1/1995 | Carr |
| 5,631,093 | A | 5/1997 | Perry et al. |
| 5,631,618 | A | 5/1997 | Trumper et al. |
| 6,072,251 | A | 6/2000 | Markle |
| 6,170,131 | B1 | 1/2001 | Shin |
| 6,275,778 | B1 | 8/2001 | Shimada et al. |
| 6,457,179 | B1 | 10/2002 | Prendergast |
| 6,607,304 | B1 | 8/2003 | Lake et al. |
| 6,720,698 | B2 | 4/2004 | Galbraith |
| 6,847,134 | B2 | 1/2005 | Frissen et al. |
| 6,862,748 | B2 | 3/2005 | Prendergast |
| 6,927,657 | B1 | 8/2005 | Wu |
| 6,971,147 | B2 | 12/2005 | Halstead |
| 7,066,778 | B2 | 6/2006 | Kretzschmar |
| 7,362,018 | B1 | 4/2008 | Kulogo et al. |
| 7,444,683 | B2 | 11/2008 | Prendergast et al. |
| 2004/0003487 | A1 | 1/2004 | Reiter |
| 2006/0066428 | A1 | 3/2006 | McCarthy et al. |
| 2006/0189259 | A1 | 8/2006 | Park |
| 2006/0290451 | A1 | 12/2006 | Prendergast et al. |
| 2008/0186683 | A1 | 8/2008 | Ligtenberg et al. |
| 2008/0272868 | A1 | 11/2008 | Prendergast et al. |
| 2008/0282517 | A1 | 11/2008 | Claro |

FOREIGN PATENT DOCUMENTS

| | | |
|---|---|---|
| WO | 2007081830 A2 | 7/2007 |

OTHER PUBLICATIONS

"Magnetic Safety Sensors" pp. 1-3, http://farnell.com/datasheets/6465.pdf (downloaded on or before Jan. 23, 2009).

"Series BNS-B20 Coded-Magnet Sensor Safety Door Handle" pp. 1-2, http://www.schmersalusa.com/catalog_pdfs/BNS_B20.pdf (downloaded on or before Jan. 23, 2009).

"Series BNS333 Coded-Magnet Sensors with Integrated Safety Control Module" pp. 1-2, http://www.schmersalusa.com/machine_guarding/coded_magnet/drawings/bns333.pdf (downloaded on or before Jan. 23, 2009).

Dr. A.D. Walmsley "Magnets in Restorative Denistry", pp. 1-9, http://priory.com/mags.htm (downloaded May 22, 2009).

* cited by examiner

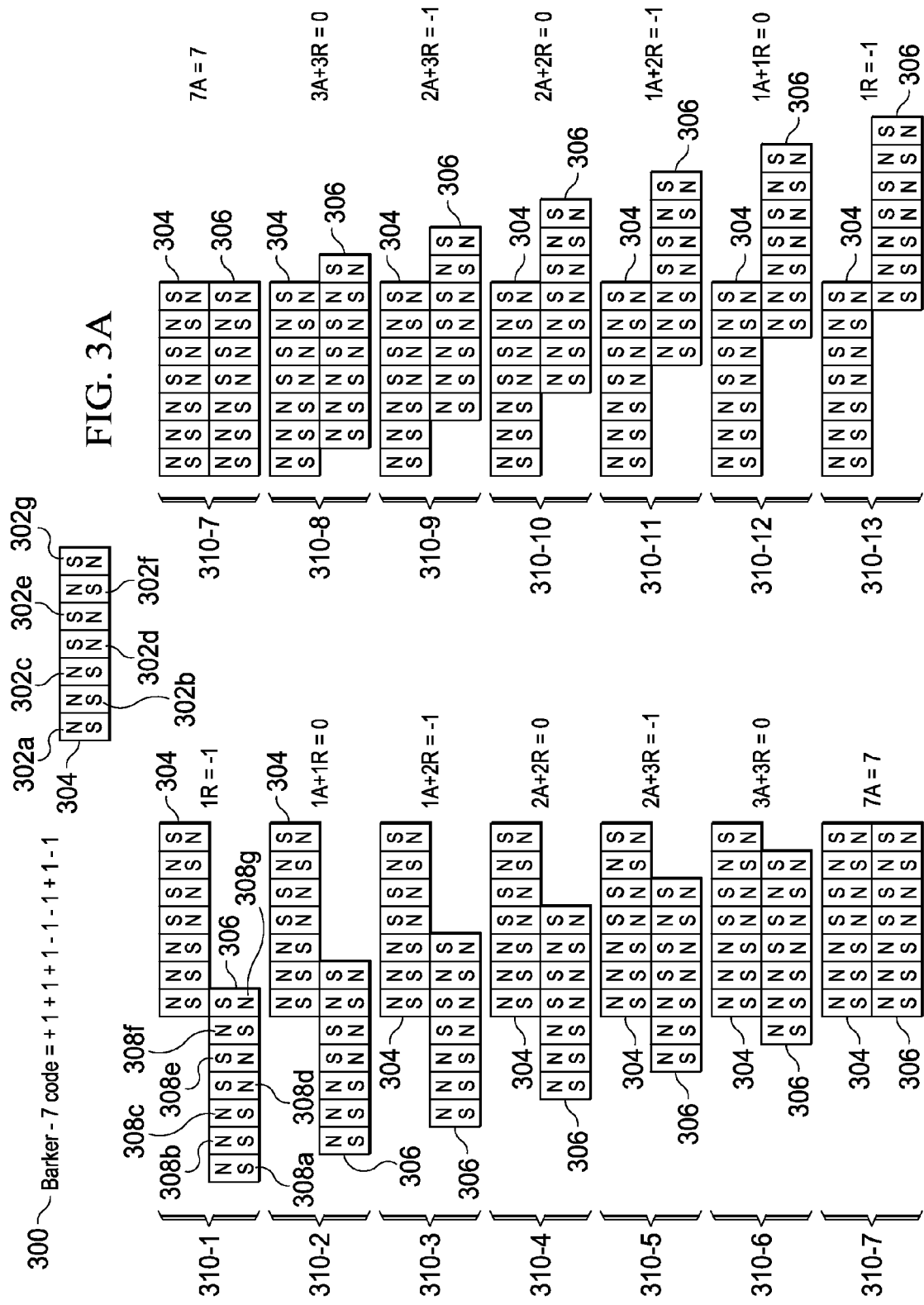

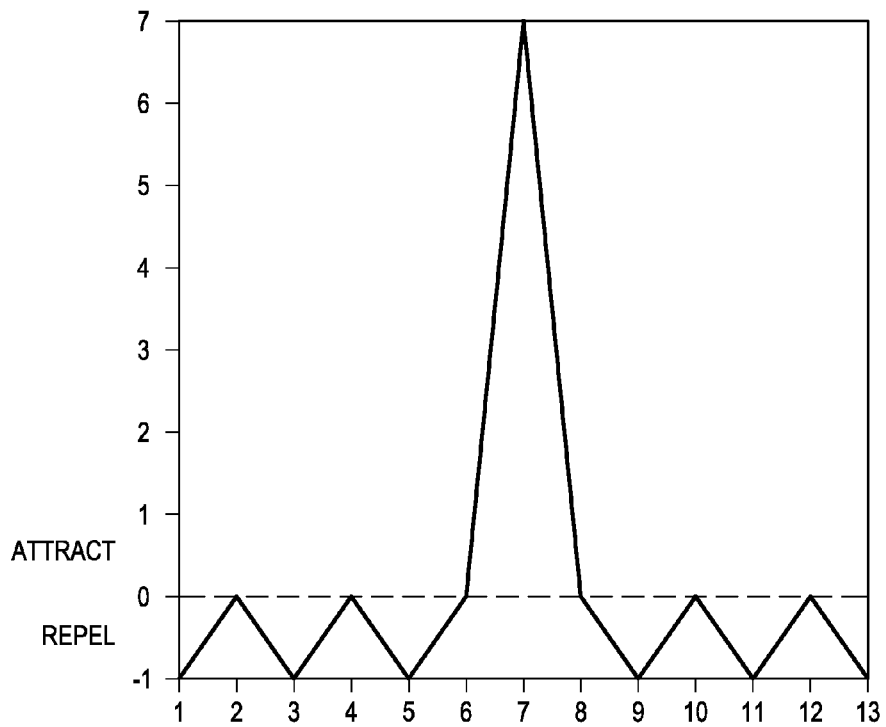
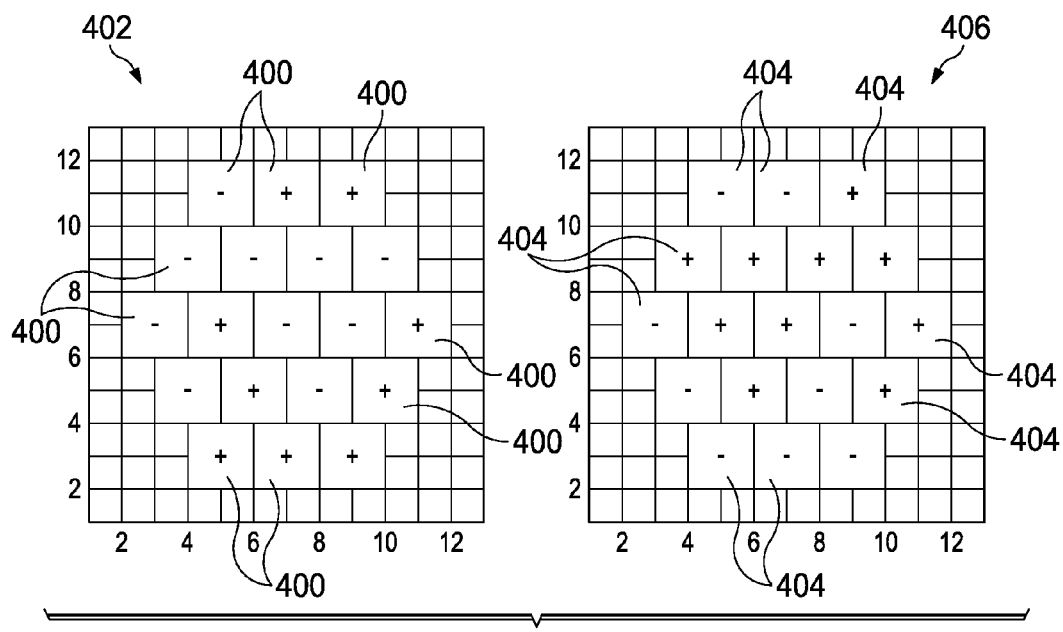
FIG. 4A

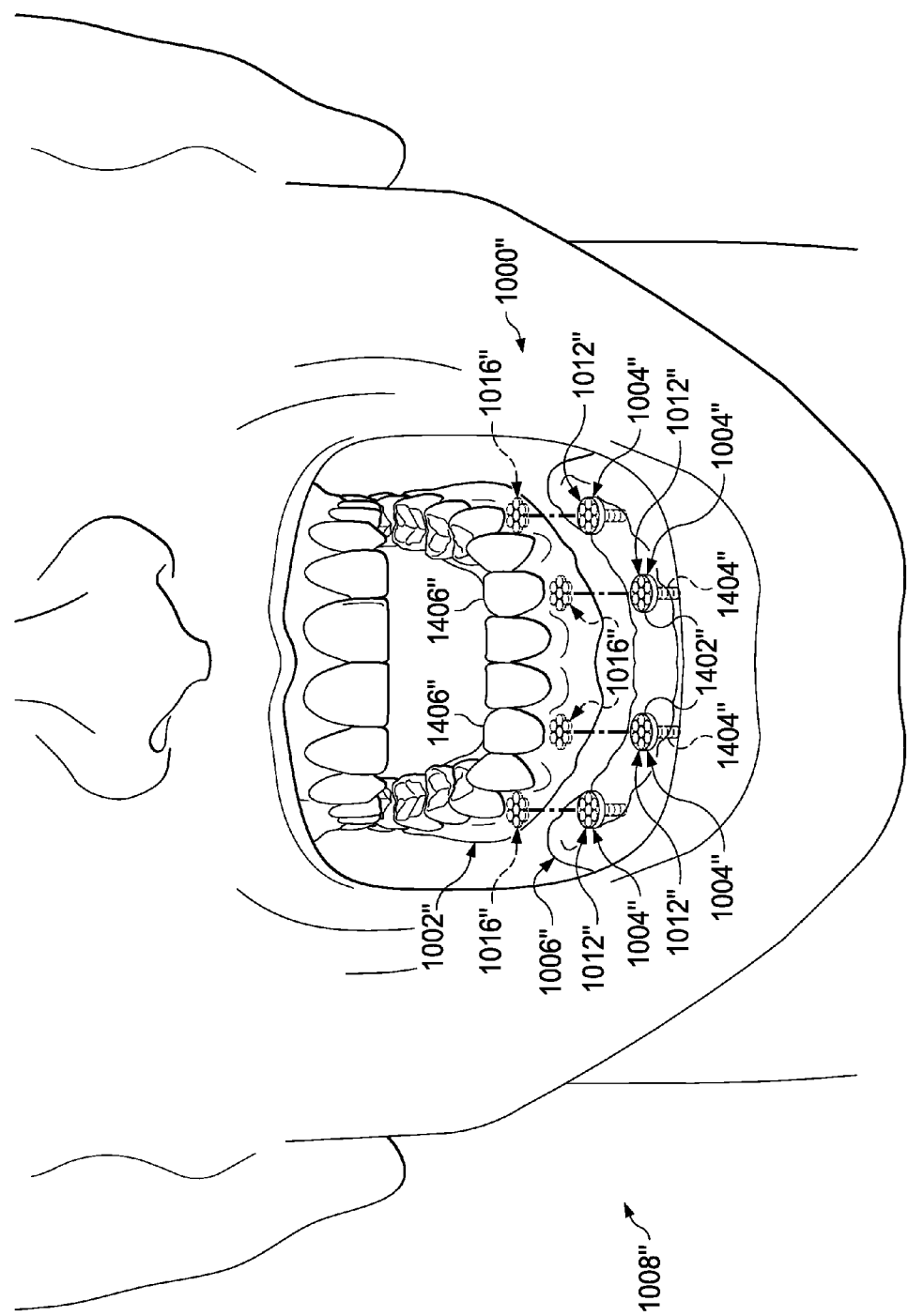

US 7,817,004 B2

CORRELATED MAGNETIC PROSTHETIC DEVICE AND METHOD FOR USING THE CORRELATED MAGNETIC PROSTHETIC DEVICE

CROSS REFERENCE TO RELATED APPLICATIONS

This application is a continuation-in-part application of U.S. patent application Ser. No. 12/476,952 filed on Jun. 2, 2009 and entitled "A Field Emission System and Method", which is a continuation-in-part application of U.S. patent application Ser. No. 12/322,561 filed on Feb. 4, 2009 and entitled "A System and Method for Producing an Electric Pulse", which is a continuation-in-part application of U.S. patent application Ser. No. 12/358,423 filed on Jan. 23, 2009 and entitled "A Field Emission System and Method", which is a continuation-in-part application of U.S. patent application Ser. No. 12/123,718 filed on May 20, 2008 and entitled "A Field Emission System and Method". The contents of these four documents are hereby incorporated herein by reference.

TECHNICAL FIELD

The present invention is related to a prosthetic device that uses correlated magnets which enable an artificial prosthesis (e.g., artificial limb) to be easily and effectively attached to and removed from an interface that is secured to a residual limb on a person. In addition, the present invention is related to a method for enabling a person to attach and remove an artificial prosthesis to and from an interface that is secured to a residual limb on the person.

DESCRIPTION OF RELATED ART

Artificial prostheses (artificial limbs) are an important part of everyday life for most amputees. For instance, leg amputees need artificial legs for mobility and arm amputees need artificial hands to help with many daily activities. Advances in prosthetic technology are continually improving artificial limbs with the goal of making life easier for the amputee. One such advancement in prosthetic technology is the subject of the present invention.

SUMMARY

In one aspect, the present invention provides a prosthetic device with an interface (e.g., prosthetic liner, keeper) which includes a first field emission structure, where the interface is secured to a residual limb on a person. The prosthetic device also has an artificial prosthesis (e.g., artificial limb) which includes a second field emission structure. The artificial prosthesis is attached to the interface when the first and second field emission structures are located next to one another and have a certain alignment with respect to one another. The first and second field emission structures each include field emission sources having positions and polarities relating to a desired spatial force function that corresponds to a relative alignment of the first and second field emission structures within a field domain. The artificial prosthesis can be released from the interface when the first and second field emission structures are turned (misaligned) with respect to one another so the person is able to remove the artificial prosthesis.

In another aspect, the present invention provides a method for enabling a person to attach and remove an artificial prosthesis (e.g., artificial limb) to and from an interface (e.g., prosthetic liner, keeper) that is secured to a residual limb on the person. The method includes the steps of: (a) securing the interface which includes a first field emission structure to the residual limb; (b) moving the artificial prosthesis which includes a second field emission structure towards the interface; and (c) aligning the first and second field emission structures so the artificial prosthesis attaches to the interface when the first and second field emission structures are located next to one another and have a certain alignment with respect to one another. The first and second field emission structures each include field emission sources having positions and polarities relating to a desired spatial force function that corresponds to a relative alignment of the first and second field emission structures within a field domain. The artificial prosthesis can be released from the interface when the first and second field emission structures are turned (misaligned) with respect to one another so the person is able to remove the artificial prosthesis.

Additional aspects of the invention will be set forth, in part, in the detailed description, figures and any claims which follow, and in part will be derived from the detailed description, or can be learned by practice of the invention. It is to be understood that both the foregoing general description and the following detailed description are exemplary and explanatory only and are not restrictive of the invention as disclosed.

BRIEF DESCRIPTION OF THE DRAWINGS

A more complete understanding of the present invention may be obtained by reference to the following detailed description when taken in conjunction with the accompanying drawings wherein:

FIGS. 1-9 are various diagrams used to help explain different concepts about correlated magnetic technology which can be utilized in an embodiment of the present invention;

FIGS. 14A-14B are several diagrams of an exemplary correlated magnetic prosthetic device (e.g., denture) in accordance with an embodiment of the present invention.

DETAILED DESCRIPTION

The present invention includes a prosthetic device that uses correlated magnets which enable an artificial limb (e.g., artificial leg, artificial arm, dentures) to be easily and effectively attached to and removed from an interface (e.g., prosthetic liner, keepers) secured to a residual limb on a person. The prosthetic device of the present invention is made possible, in part, by the use of an emerging, revolutionary technology that is called correlated magnetics. This revolutionary technology referred to herein as correlated magnetics was first fully described and enabled in the co-assigned U.S. patent application Ser. No. 12/123,718 filed on May 20, 2008 and entitled "A Field Emission System and Method". The contents of this document are hereby incorporated herein by reference. A second generation of a correlated magnetic technology is described and enabled in the co-assigned U.S. patent application Ser. No. 12/358,423 filed on Jan. 23, 2009 and entitled "A Field Emission System and Method". The contents of this document are hereby incorporated herein by reference. A third generation of a correlated magnetic technology is described and enabled in the co-assigned U.S. patent application Ser. No. 12/476,952 filed on Jun. 2, 2009 and entitled "A Field Emission System and Method". The contents of this document are hereby incorporated herein by reference. Another technology known as correlated inductance, which is related to correlated magnetics, has been described and enabled in the co-assigned U.S. patent application Ser. No. 12/322,561 filed on Feb. 4, 2009 and entitled "A System and Method for Producing an Electric Pulse". The contents of this document are hereby incorporated by reference. A brief discussion about correlated magnetics is provided first before a detailed discussion is provided about the correlated magnetic prosthetic device and method of the present invention.

Correlated Magnetics Technology

This section is provided to introduce the reader to basic magnets and the new and revolutionary correlated magnetic technology. This section includes subsections relating to basic magnets, correlated magnets, and correlated electromagnetics. It should be understood that this section is provided to assist the reader with understanding the present invention, and should not be used to limit the scope of the present invention.

A. Magnets

Figure 1:
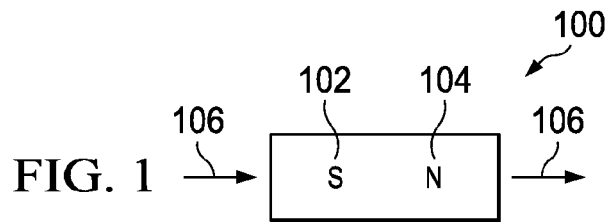

A magnet is a material or object that produces a magnetic field which is a vector field that has a direction and a magnitude (also called strength). Referring to FIG. 1, there is illustrated an exemplary magnet 100 which has a South pole 102 and a North pole 104 and magnetic field vectors 106 that represent the direction and magnitude of the magnet's moment. The magnet's moment is a vector that characterizes the overall magnetic properties of the magnet 100. For a bar magnet, the direction of the magnetic moment points from the South pole 102 to the North pole 104. The North and South poles 104 and 102 are also referred to herein as positive (+) and negative (−) poles, respectively.

Figure 2A:
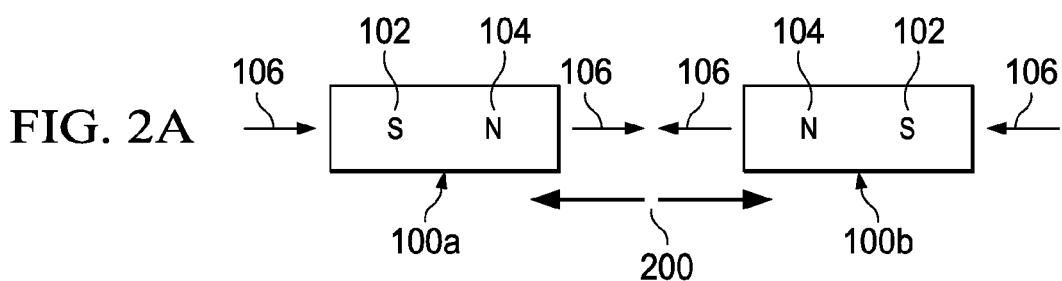
Figure 2B:
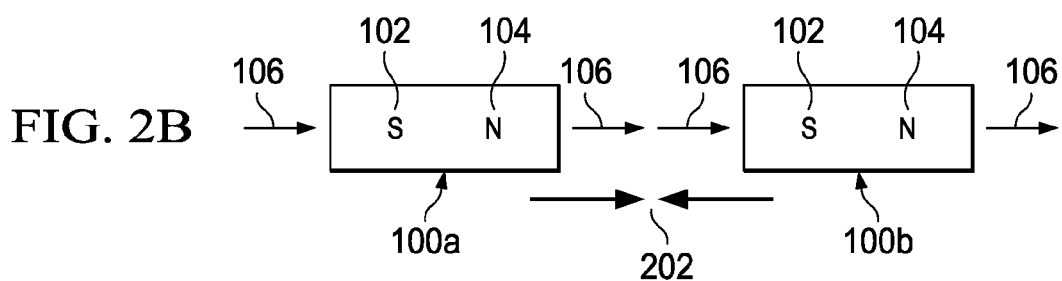
Figure 2C:
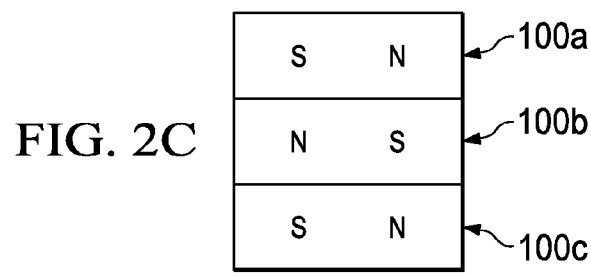

Referring to FIG. 2A, there is a diagram that depicts two magnets 100a and 100b aligned such that their polarities are opposite in direction resulting in a repelling spatial force 200 which causes the two magnets 100a and 100b to repel each other. In contrast, FIG. 2B is a diagram that depicts two magnets 100a and 100b aligned such that their polarities are in the same direction resulting in an attracting spatial force 202 which causes the two magnets 100a and 100b to attract each other. In FIG. 2B, the magnets 100a and 100b are shown as being aligned with one another but they can also be partially aligned with one another where they could still "stick" to each other and maintain their positions relative to each other. FIG. 2C is a diagram that illustrates how magnets 100a, 100b and 100c will naturally stack on one another such that their poles alternate.

B. Correlated Magnets

Correlated magnets can be created in a wide variety of ways depending on the particular application as described in the aforementioned U.S. patent applications Ser. No. 12/123,718, 12/358,432, and 12/476,952 by using a unique combination of magnet arrays (referred to herein as magnetic field emission sources), correlation theory (commonly associated with probability theory and statistics) and coding theory (commonly associated with communication systems). A brief discussion is provided next to explain how these widely diverse technologies are used in a unique and novel way to create correlated magnets.

Basically, correlated magnets are made from a combination of magnetic (or electric) field emission sources which have been configured in accordance with a pre-selected code having desirable correlation properties. Thus, when a magnetic field emission structure is brought into alignment with a complementary, or mirror image, magnetic field emission structure the various magnetic field emission sources will all align causing a peak spatial attraction force to be produced, while the misalignment of the magnetic field emission structures cause the various magnetic field emission sources to substantially cancel each other out in a manner that is a function of the particular code used to design the two magnetic field emission structures. In contrast, when a magnetic field emission structure is brought into alignment with a duplicate magnetic field emission structure then the various magnetic field emission sources all align causing a peak spatial repelling force to be produced, while the misalignment of the magnetic field emission structures causes the various magnetic field emission sources to substantially cancel each other out in a manner that is a function of the particular code used to design the two magnetic field emission structures.

The aforementioned spatial forces (attraction, repelling) have a magnitude that is a function of the relative alignment of two magnetic field emission structures and their corresponding spatial force (or correlation) function, the spacing (or distance) between the two magnetic field emission structures, and the magnetic field strengths and polarities of the various sources making up the two magnetic field emission structures. The spatial force functions can be used to achieve precision alignment and precision positioning not possible with basic magnets. Moreover, the spatial force functions can enable the precise control of magnetic fields and associated spatial forces thereby enabling new forms of attachment devices for attaching objects with precise alignment and new systems and methods for controlling precision movement of objects. An additional unique characteristic associated with correlated magnets relates to the situation where the various magnetic field sources making-up two magnetic field emission structures can effectively cancel out each other when they are brought out of alignment which is described herein as a release force. This release force is a direct result of the particular correlation coding used to configure the magnetic field emission structures.

A person skilled in the art of coding theory will recognize that there are many different types of codes that have different correlation properties which have been used in communications for channelization purposes, energy spreading, modulation, and other purposes. Many of the basic characteristics of such codes make them applicable for use in producing the magnetic field emission structures described herein. For example, Barker codes are known for their autocorrelation properties and can be used to help configure correlated magnets. Although, a Barker code is used in an example below with respect to FIGS. 3A-3B, other forms of codes which may or may not be well known in the art are also applicable to correlated magnets because of their autocorrelation, cross-correlation, or other properties including, for example, Gold codes, Kasami sequences, hyperbolic congruential codes, quadratic congruential codes, linear congruential codes, Welch-Costas array codes, Golomb-Costas array codes, pseudorandom codes, chaotic codes, Optimal Golomb Ruler codes, deterministic codes, designed codes, one dimensional codes, two dimensional codes, three dimensional codes, or four dimensional codes, combinations thereof, and so forth.

Referring to FIG. 3A, there are diagrams used to explain how a Barker length 7 code 300 can be used to determine polarities and positions of magnets 302a, 302b . . . 302g making up a first magnetic field emission structure 304. Each magnet 302a, 302b . . . 302g has the same or substantially the same magnetic field strength (or amplitude), which for the sake of this example is provided as a unit of I (where A=Attract, R=Repel, A=−R, A=1, R=−1). A second magnetic field emission structure 306 (including magnets 308a, 308b . . . 308g) that is identical to the first magnetic field emission structure 304 is shown in 13 different alignments 310-1 through 310-13 relative to the first magnetic field emission structure 304. For each relative alignment, the number of magnets that repel plus the number of magnets that attract is calculated, where each alignment has a spatial force in accordance with a spatial force function based upon the correlation function and magnetic field strengths of the magnets 302a, 302b . . . 302g and 308a, 308b . . . 308g. With the specific Barker code used, the spatial force varies from −1 to 7, where the peak occurs when the two magnetic field emission structures 304 and 306 are aligned which occurs when their respective codes are aligned. The off peak spatial force, referred to as a side lobe force, varies from 0 to −1. As such, the spatial force function causes the magnetic field emission structures 304 and 306 to generally repel each other unless they are aligned such that each of their magnets are correlated with a complementary magnet (i.e., a magnet's South pole aligns with another magnet's North pole, or vice versa). In other words, the two magnetic field emission structures 304 and 306 substantially correlate with one another when they are aligned to substantially mirror each other.

In FIG. 3B, there is a plot that depicts the spatial force function of the two magnetic field emission structures 304 and 306 which results from the binary autocorrelation function of the Barker length 7 code 300, where the values at each alignment position 1 through 13 correspond to the spatial force values that were calculated for the thirteen alignment positions 310-1 through 310-13 between the two magnetic field emission structures 304 and 306 depicted in FIG. 3A. As the true autocorrelation function for correlated magnet field structures is repulsive, and most of the uses envisioned will have attractive correlation peaks, the usage of the term 'autocorrelation' herein will refer to complementary correlation unless otherwise stated. That is, the interacting faces of two such correlated magnetic field emission structures 304 and 306 will be complementary to (i.e., mirror images of) each other. This complementary autocorrelation relationship can be seen in FIG. 3A where the bottom face of the first magnetic field emission structure 304 having the pattern 'S S S N N S N' is shown interacting with the top face of the second magnetic field emission structure 306 having the pattern 'N N N S S N S', which is the mirror image (pattern) of the bottom face of the first magnetic field emission structure 304.

Figure 4B:
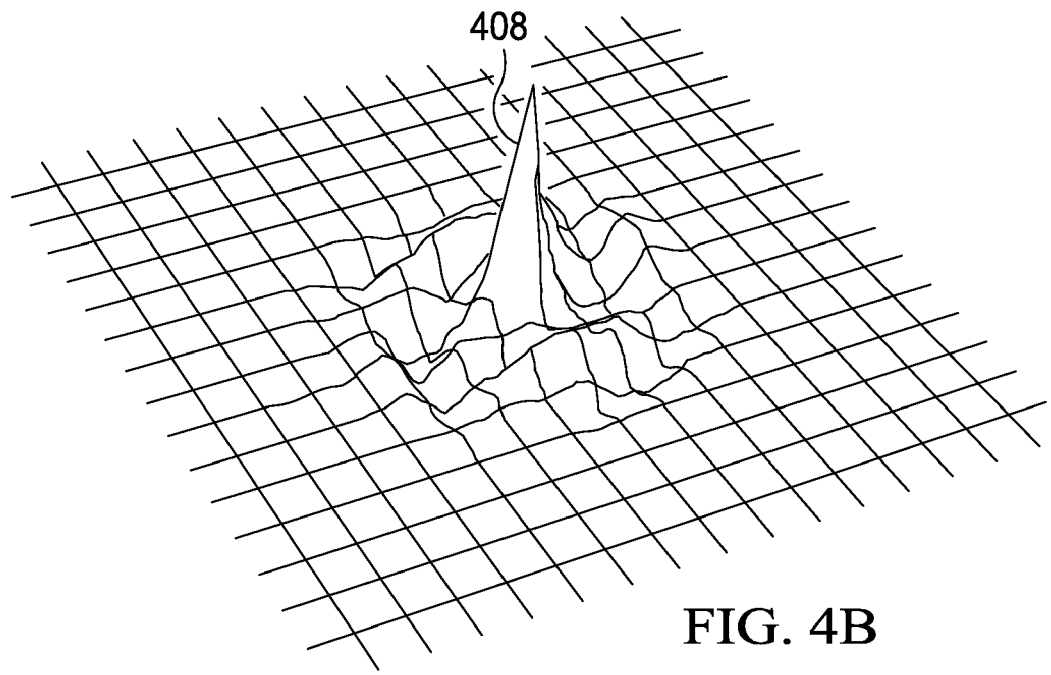
Figure 4C:
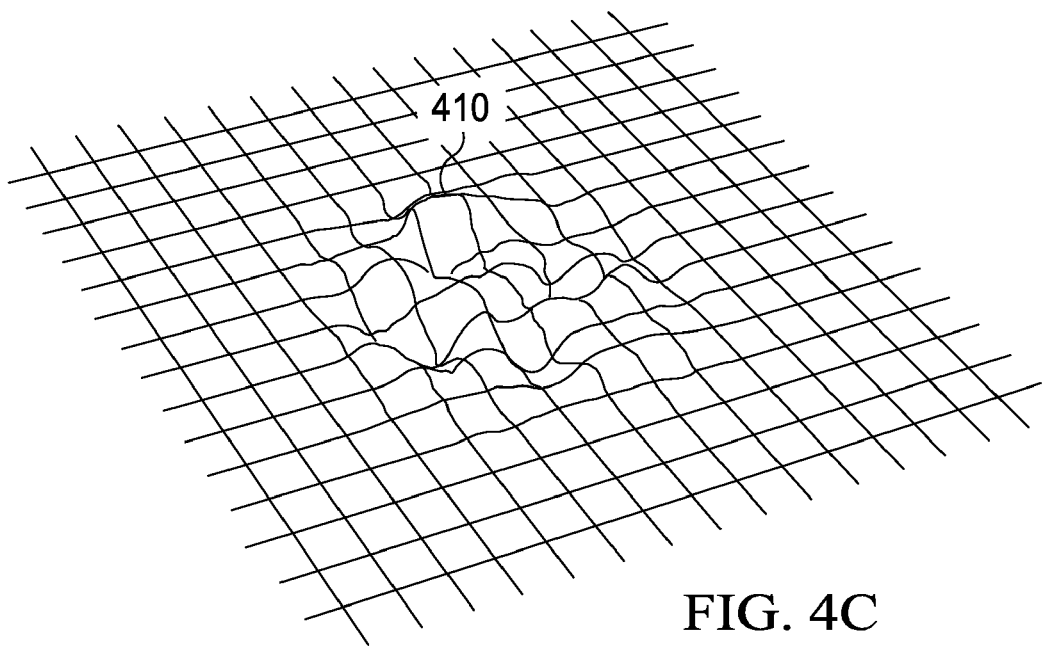

Referring to FIG. 4A, there is a diagram of an array of 19 magnets 400 positioned in accordance with an exemplary code to produce an exemplary magnetic field emission structure 402 and another array of 19 magnets 404 which is used to produce a mirror image magnetic field emission structure 406. In this example, the exemplary code was intended to produce the first magnetic field emission structure 402 to have a first stronger lock when aligned with its mirror image magnetic field emission structure 406 and a second weaker lock when it is rotated 90° relative to its mirror image magnetic field emission structure 406. FIG. 4B depicts a spatial force function 408 of the magnetic field emission structure 402 interacting with its mirror image magnetic field emission structure 406 to produce the first stronger lock. As can be seen, the spatial force function 408 has a peak which occurs when the two magnetic field emission structures 402 and 406 are substantially aligned. FIG. 4C depicts a spatial force function 410 of the magnetic field emission structure 402 interacting with its mirror magnetic field emission structure 406 after being rotated 90°. As can be seen, the spatial force function 410 has a smaller peak which occurs when the two magnetic field emission structures 402 and 406 are substantially aligned but one structure is rotated 90°. If the two magnetic field emission structures 402 and 406 are in other positions then they could be easily separated.

Figure 5:
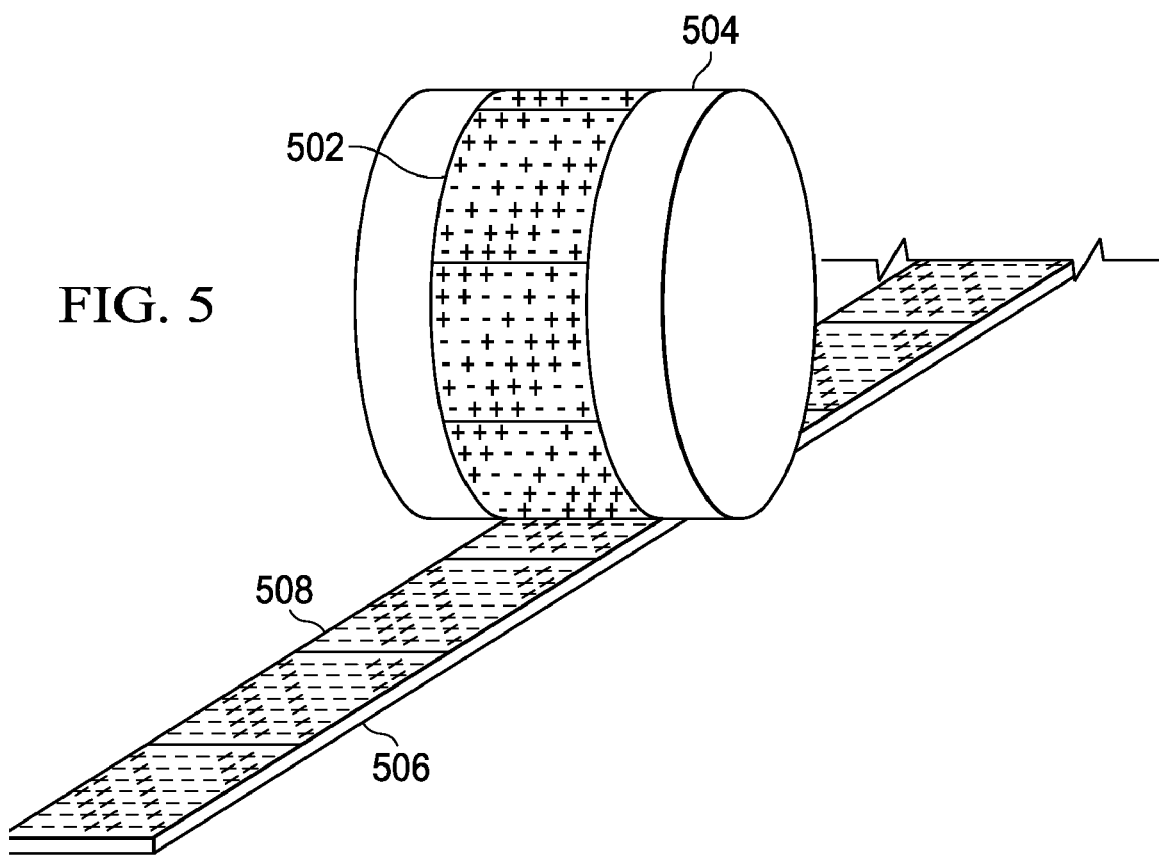

Referring to FIG. 5, there is a diagram depicting a correlating magnet surface 502 being wrapped back on itself on a cylinder 504 (or disc 504, wheel 504) and a conveyor belt/tracked structure 506 having located thereon a mirror image correlating magnet surface 508. In this case, the cylinder 504 can be turned clockwise or counterclockwise by some force so as to roll along the conveyor belt/tracked structure 506. The fixed magnetic field emission structures 502 and 508 provide a traction and gripping (i.e., holding) force as the cylinder 504 is turned by some other mechanism (e.g., a motor). The gripping force would remain substantially constant as the cylinder 504 moved down the conveyor belt/tracked structure 506 independent of friction or gravity and could therefore be used to move an object about a track that moved up a wall, across a ceiling, or in any other desired direction within the limits of the gravitational force (as a function of the weight of the object) overcoming the spatial force of the aligning magnetic field emission structures 502 and 508. If desired, this cylinder 504 (or other rotary devices) can also be operated against other rotary correlating surfaces to provide a gear-like operation. Since the hold-down force equals the traction force, these gears can be loosely connected and still give positive, non-slipping rotational accuracy. Plus, the magnetic field emission structures 502 and 508 can have surfaces which are perfectly smooth and still provide positive, non-slip traction. In contrast to legacy friction-based wheels, the traction force provided by the magnetic field emission structures 502 and 508 is largely independent of the friction forces between the traction wheel and the traction surface and can be employed with low friction surfaces. Devices moving about based on magnetic traction can be operated independently of gravity for example in weightless conditions including space, underwater, vertical surfaces and even upside down.

Figure 6:
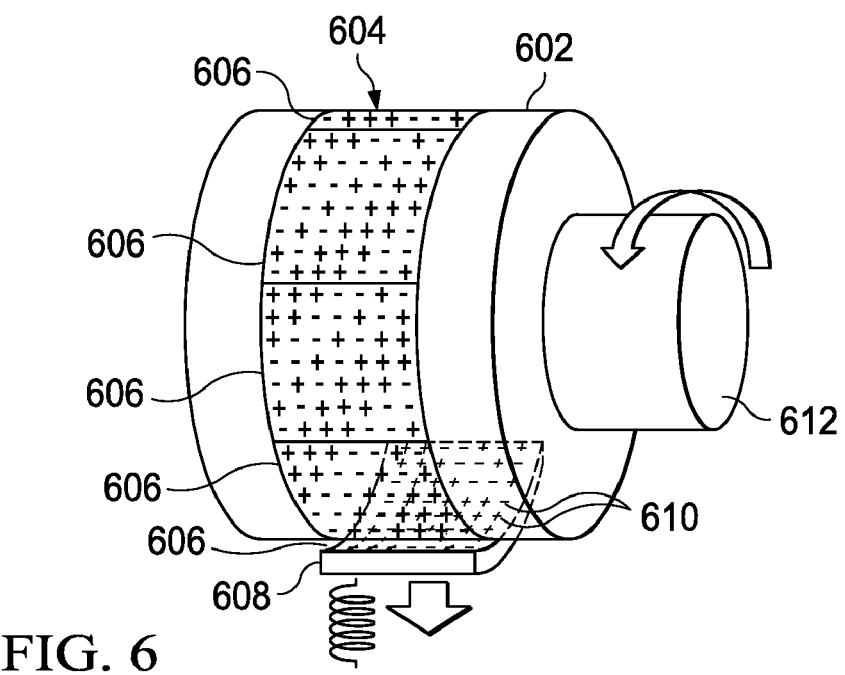

Referring to FIG. 6, there is a diagram depicting an exemplary cylinder 602 having wrapped thereon a first magnetic field emission structure 604 with a code pattern 606 that is repeated six times around the outside of the cylinder 602. Beneath the cylinder 602 is an object 608 having a curved surface with a slightly larger curvature than the cylinder 602 and having a second magnetic field emission structure 610 that is also coded using the code pattern 606. Assume, the cylinder 602 is turned at a rotational rate of 1 rotation per second by shaft 612. Thus, as the cylinder 602 turns, six times a second the first magnetic field emission structure 604 on the cylinder 602 aligns with the second magnetic field emission structure 610 on the object 608 causing the object 608 to be repelled (i.e., moved downward) by the peak spatial force function of the two magnetic field emission structures 604 and 610. Similarly, had the second magnetic field emission structure 610 been coded using a code pattern that mirrored code pattern 606, then 6 times a second the first magnetic field emission structure 604 of the cylinder 602 would align with the second magnetic field emission structure 610 of the object 608 causing the object 608 to be attracted (i.e., moved upward) by the peak spatial force function of the two magnetic field emission structures 604 and 610. Thus, the movement of the cylinder 602 and the corresponding first magnetic field emission structure 604 can be used to control the movement of the object 608 having its corresponding second magnetic field emission structure 610. One skilled in the art will recognize that the cylinder 602 may be connected to a shaft 612 which may be turned as a result of wind turning a windmill, a water wheel or turbine, ocean wave movement, and other methods whereby movement of the object 608 can result from some source of energy scavenging. As such, correlated magnets enables the spatial forces between objects to be precisely controlled in accordance with their movement and also enables the movement of objects to be precisely controlled in accordance with such spatial forces.

In the above examples, the correlated magnets 304, 306, 402, 406, 502, 508, 604 and 610 overcome the normal 'magnet orientation' behavior with the aid of a holding mechanism such as an adhesive, a screw, a bolt & nut, etc. . . . In other cases, magnets of the same magnetic field emission structure could be sparsely separated from other magnets (e.g., in a sparse array) such that the magnetic forces of the individual magnets do not substantially interact, in which case the polarity of individual magnets can be varied in accordance with a code without requiring a holding mechanism to prevent magnetic forces from 'flipping' a magnet. However, magnets are typically close enough to one another such that their magnetic forces would substantially interact to cause at least one of them to 'flip' so that their moment vectors align but these magnets can be made to remain in a desired orientation by use of a holding mechanism such as an adhesive, a screw, a bolt & nut, etc. . . . As such, correlated magnets often utilize some sort of holding mechanism to form different magnetic field emission structures which can be used in a wide-variety of applications like, for example, a turning mechanism, a tool insertion slot, alignment marks, a latch mechanism, a pivot mechanism, a swivel mechanism, a lever, a drill head assembly, a hole cutting tool assembly, a machine press tool, a gripping apparatus, a slip ring mechanism, and a structural assembly.

C. Correlated Electromagnetics

Correlated magnets can entail the use of electromagnets which is a type of magnet in which the magnetic field is produced by the flow of an electric current. The polarity of the magnetic field is determined by the direction of the electric current and the magnetic field disappears when the current ceases. Following are a couple of examples in which arrays of electromagnets are used to produce a first magnetic field emission structure that is moved over time relative to a second magnetic field emission structure which is associated with an object thereby causing the object to move.

Figure 7:
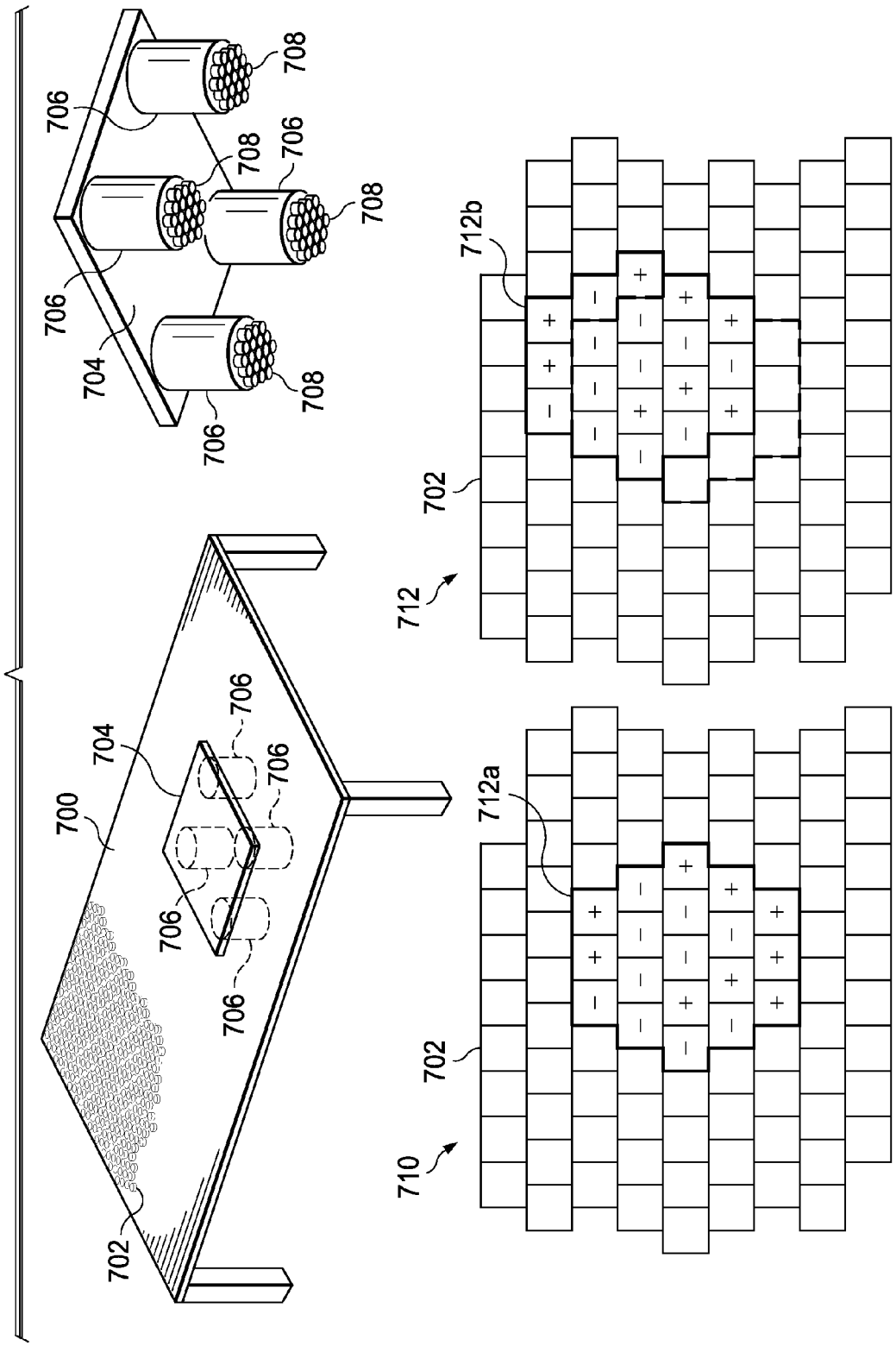

Referring to FIG. 7, there are several diagrams used to explain a 2-D correlated electromagnetics example in which there is a table 700 having a two-dimensional electromagnetic array 702 (first magnetic field emission structure 702) beneath its surface and a movement platform 704 having at least one table contact member 706. In this example, the movement platform 704 is shown having four table contact members 706 each having a magnetic field emission structure 708 (second magnetic field emission structures 708) that would be attracted by the electromagnetic array 702. Computerized control of the states of individual electromagnets of the electromagnet array 702 determines whether they are on or off and determines their polarity. A first example 710 depicts states of the electromagnetic array 702 configured to cause one of the table contact members 706 to attract to a subset 712a of the electromagnets within the magnetic field emission structure 702. A second example 712 depicts different states of the electromagnetic array 702 configured to cause the one table contact member 706 to be attracted (i.e., move) to a different subset 712b of the electromagnets within the field emission structure 702. Per the two examples, one skilled in the art can recognize that the table contact member(s) 706 can be moved about table 700 by varying the states of the electromagnets of the electromagnetic array 702.

Figure 8:
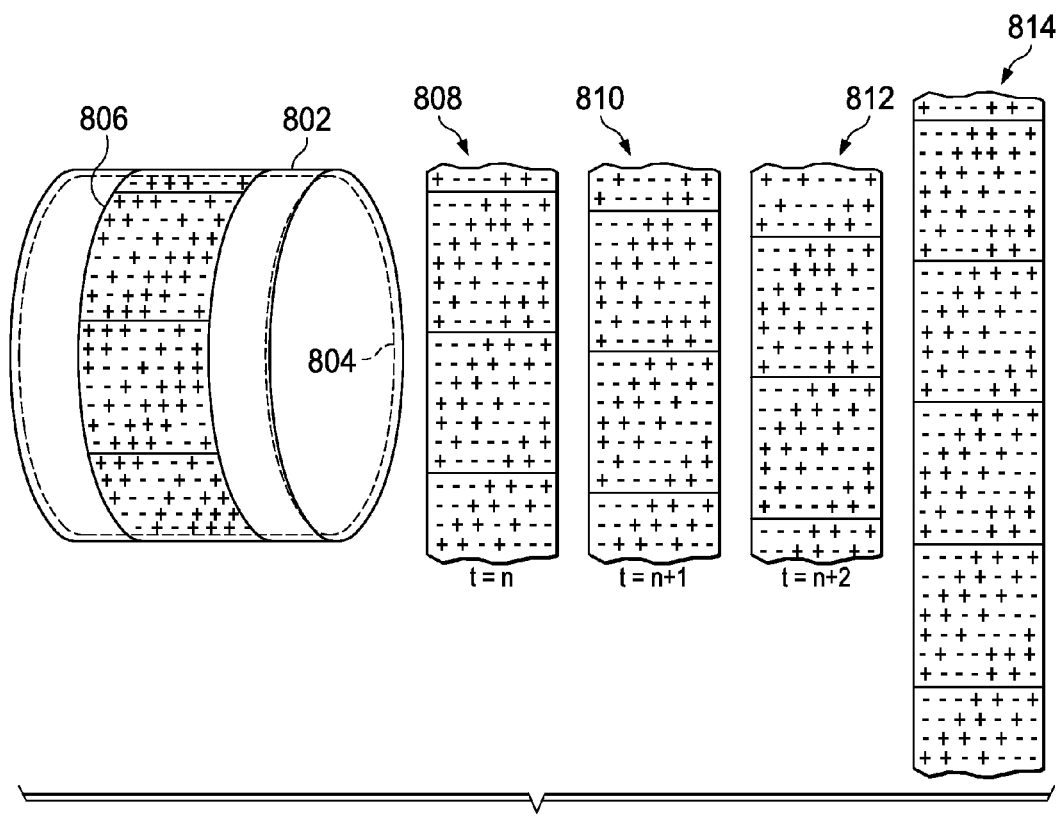

Referring to FIG. 8, there are several diagrams used to explain a 3-D correlated electromagnetics example where there is a first cylinder 802 which is slightly larger than a second cylinder 804 that is contained inside the first cylinder 802. A magnetic field emission structure 806 is placed around the first cylinder 802 (or optionally around the second cylinder 804). An array of electromagnets (not shown) is associated with the second cylinder 804 (or optionally the first cylinder 802) and their states are controlled to create a moving mirror image magnetic field emission structure to which the magnetic field emission structure 806 is attracted so as to cause the first cylinder 802 (or optionally the second cylinder 804) to rotate relative to the second cylinder 804 (or optionally the first cylinder 802). The magnetic field emission structures 808, 810, and 812 produced by the electromagnetic array on the second cylinder 804 at time t=n, t=n+1, and t=n+2, show a pattern mirroring that of the magnetic field emission structure 806 around the first cylinder 802. The pattern is shown moving downward in time so as to cause the first cylinder 802 to rotate counterclockwise. As such, the speed and direction of movement of the first cylinder 802 (or the second cylinder 804) can be controlled via state changes of the electromagnets making up the electromagnetic array. Also depicted in FIG. 8 there is an electromagnetic array 814 that corresponds to a track that can be placed on a surface such that a moving mirror image magnetic field emission structure can be used to move the first cylinder 802 backward or forward on the track using the same code shift approach shown with magnetic field emission structures 808, 810, and 812 (compare to FIG. 5).

Figure 9:
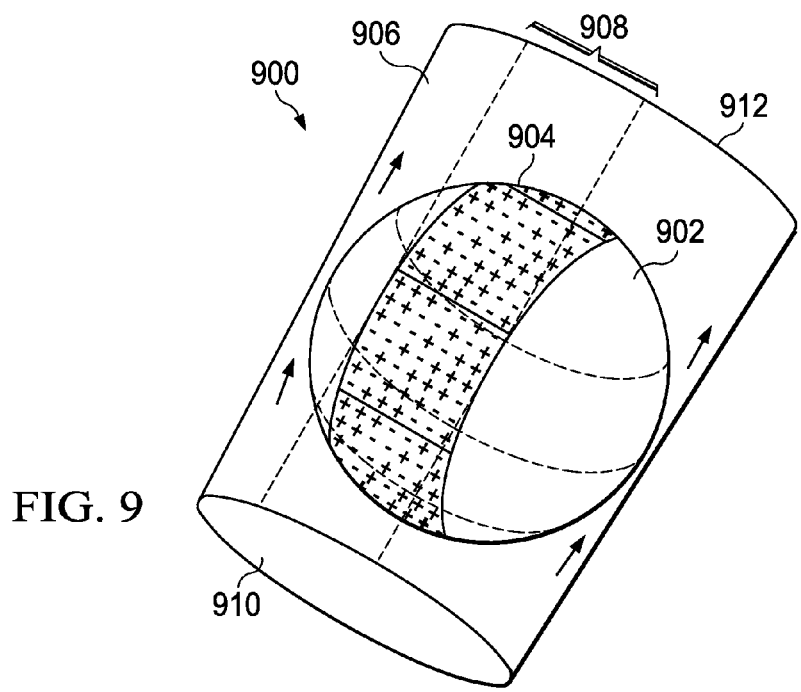

Referring to FIG. 9, there is illustrated an exemplary valve mechanism 900 based upon a sphere 902 (having a magnetic field emission structure 904 wrapped thereon) which is located in a cylinder 906 (having an electromagnetic field emission structure 908 located thereon). In this example, the electromagnetic field emission structure 908 can be varied to move the sphere 902 upward or downward in the cylinder 906 which has a first opening 910 with a circumference less than or equal to that of the sphere 902 and a second opening 912 having a circumference greater than the sphere 902. This configuration is desirable since one can control the movement of the sphere 902 within the cylinder 906 to control the flow rate of a gas or liquid through the valve mechanism 900. Similarly, the valve mechanism 900 can be used as a pressure control valve. Furthermore, the ability to move an object within another object having a decreasing size enables various types of sealing mechanisms that can be used for the sealing of windows, refrigerators, freezers, food storage containers, boat hatches, submarine hatches, etc., where the amount of sealing force can be precisely controlled. One skilled in the art will recognize that many different types of seal mechanisms that include gaskets, o-rings, and the like can be employed with the use of the correlated magnets. Plus, one skilled in the art will recognize that the magnetic field emission structures can have an array of sources including, for example, a permanent magnet, an electromagnet, an electret, a magnetized ferromagnetic material, a portion of a magnetized ferromagnetic material, a soft magnetic material, or a superconductive magnetic material, some combination thereof, and so forth.

Correlated Magnetic Prosthetic Device

Figure 10A:
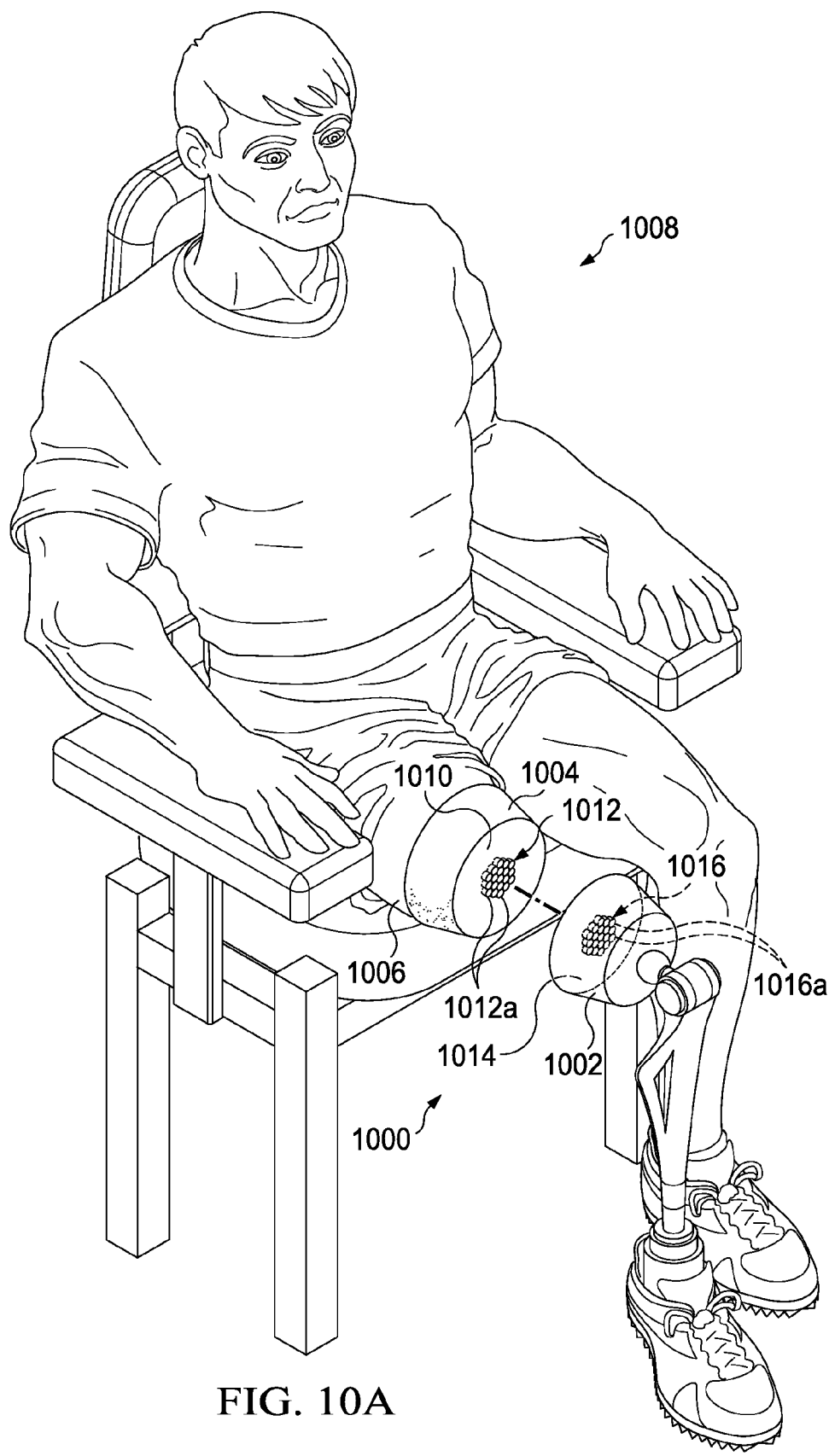
FIGS. 10A-10B are several diagrams of an exemplary correlated magnetic prosthetic device (e.g., artificial leg) in accordance with an embodiment of the present invention.
Figure 10B:
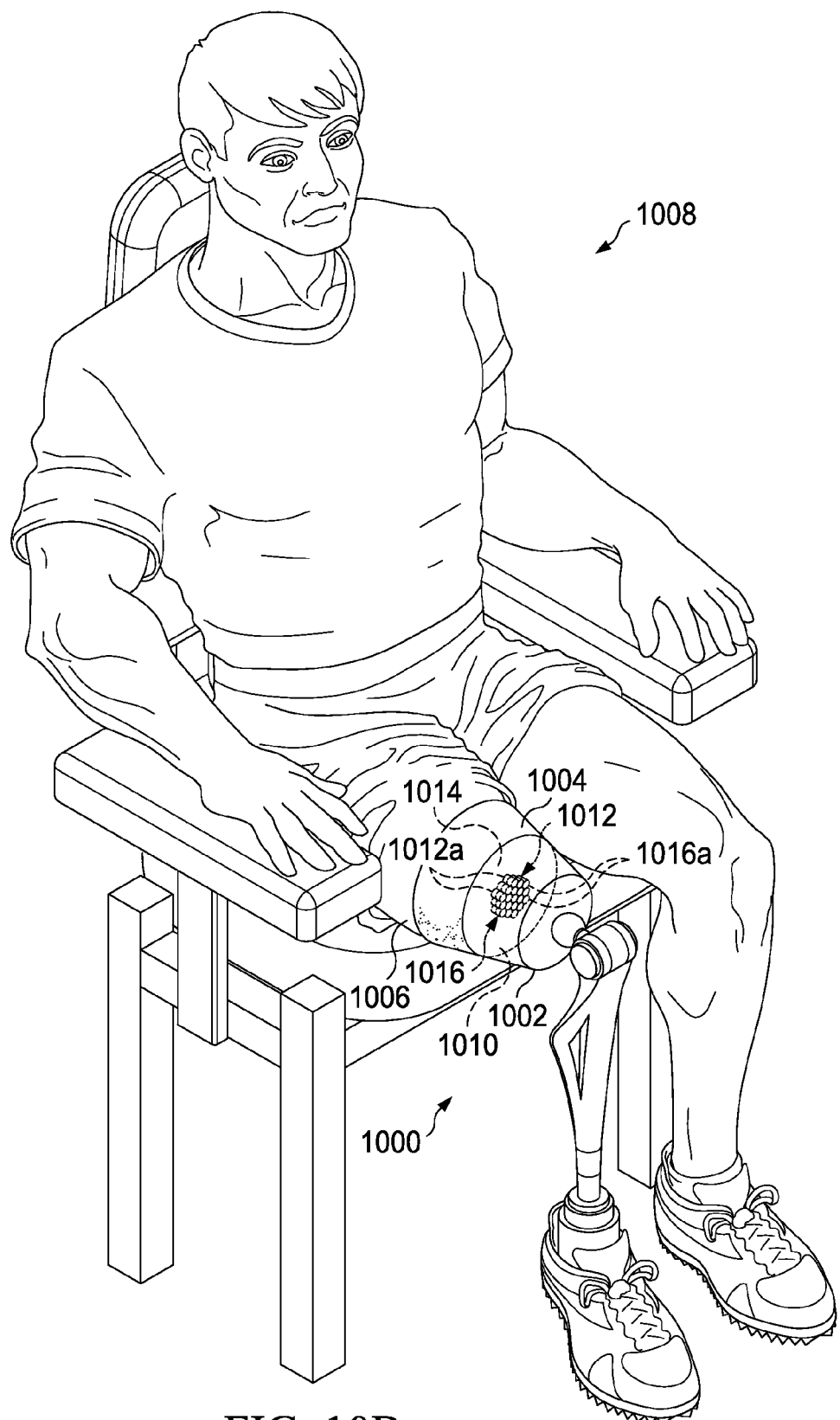

Referring to FIGS. 10A-10B, there are several diagrams of an exemplary prosthetic device 1000 which has a correlated magnetic artificial prosthesis 1002 (e.g., artificial leg 1002) that can be easily and effectively attached to and removed from a correlated magnetic interface 1004 (e.g., prosthetic liner 1004) which is secured to a residual limb 1006 on a person 1008 in accordance with an embodiment of the present invention. In this example, the interface 1004 is configured as a prosthetic liner but could be what is referred to herein as a keeper where both act as the point of contact between the person's residual limb 1006 and the artificial prosthesis 1002. The interface 1004 has a bottom surface 1010 on which there is attached a first field emission structure 1012 (more possible). In this example, the first field emission structure 1012 is shown extending outwards from the bottom surface 1010 of the interface 1004. Alternatively, the first field emission structure 1012 could be flush with the bottom surface 1010 of the interface 1004. Or, the first field emission structure 1012 could be recessed within the bottom surface 1012 of the interface 1004 such that it is not visible.

In this example, the artificial prosthesis 1002 is configured as an artificial leg but could be any type of artificial limb such as, for example, an artificial arm, an artificial hand, or an artificial foot. The artificial prosthesis 1002 has an upper surface 1014 on which there is attached a second field emission structure 1016 (more possible). In this example, the second field emission structure 1016 is shown as extending up from the upper surface 1014 of the artificial prosthesis 1002. Alternatively, the second field emission structure 1016 could be flush with the upper surface 1014 of the artificial prosthesis 1002. Or, the second field emission structure 1016 could be recessed within the upper surface 1014 of the artificial prosthesis 1002 such that it is not visible. The first and second field emission structures 1012 and 1016 depicted in FIGS. 10A-10B and in other drawings associated with the other exemplary correlated prosthetic devices 1000', 1000'', 1000a, 1000b . . . 1000o are themselves exemplary. Generally, the field emission structures 1012 and 1016 could have many different configurations and could be many different types of permanent magnets, electromagnets, and/or electro-permanent magnets where their size, shape, source strengths, coding, and other characteristics can be tailored to meet different requirements.

The first magnetic field emission structure 1012 is configured to interact (correlate) with the second magnetic field emission structure 1016 such that the artificial prosthesis 1002 can, when desired, be substantially aligned to become attached (secured) to the interface 1004 or misaligned to become removed (detached) from the interface 1004. In particular, the artificial prosthesis 1002 can be attached to the interface 1004 when their respective first and second magnetic field emission structures 1012 and 1016 are located next to one another and have a certain alignment with respect to one another (see FIG. 10B). Under one arrangement, the artificial prosthesis 1002 would be attached to the interface 1004 with a desired strength to prevent the artificial prosthesis 1002 from being inadvertently disengaged from the interface 1004. Of course, the interface 1004 would have to be properly fitted and aligned on the residual limb 1006 so that the artificial prosthesis 1002 would be properly aligned on the person 1008. The artificial prosthesis 1002 can be released from the interface 1004 when their respective first and second magnetic field emission structures 1012 and 1016 are turned relative to one another (see FIG. 10A).

The process of attaching and detaching the artificial prosthesis 1002 to and from the interface 1004 is possible because the first and second magnetic field emission structures 1012 and 1016 each include an array of field emission sources 1012a and 1016a (e.g., an array of magnets 1012a and 1016a) and each array has sources with positions and polarities relating to a desired spatial force function that corresponds to a relative alignment of the first and second magnetic field emission structures 1012 and 1016 within a field domain (see discussion about correlated magnet technology). In this example, the first and second magnetic field emissions structures 1012 and 1016 both have the same code but are a mirror image of one another (see FIGS. 4 and 11). An example of how the artificial prosthesis 1002 can be attached (secured) to or removed from the interface 1004 is discussed in detail below with respect to FIGS. 11A-11I.

Figure 11A:
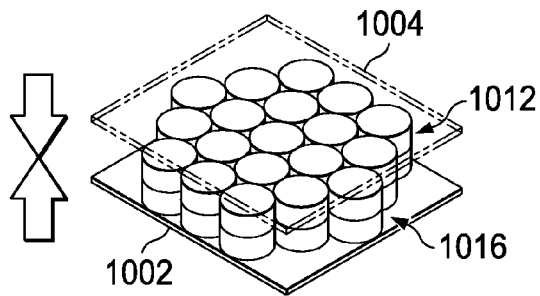
FIGS. 11A-11I are several diagrams that illustrate a portion of the prosthetic device shown in FIGS. 10A-10B which are used to show how an exemplary first magnetic field emission structure (associated with an interface) and its mirror image second magnetic field emission structure (associated with an artificial prosthesis) can be aligned or misaligned relative to each other to enable a person to secure or remove the artificial prosthesis to or from the interface which is attached to their residual limb in accordance with an embodiment of the present invention.
Figure 11D:
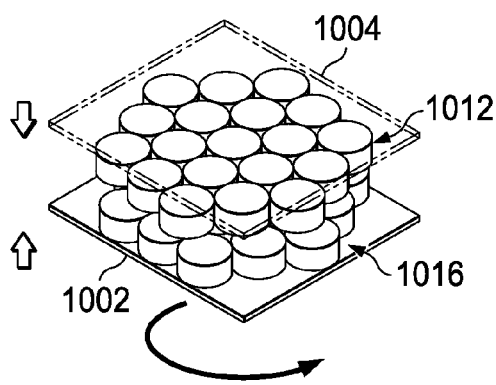
Figure 11B:
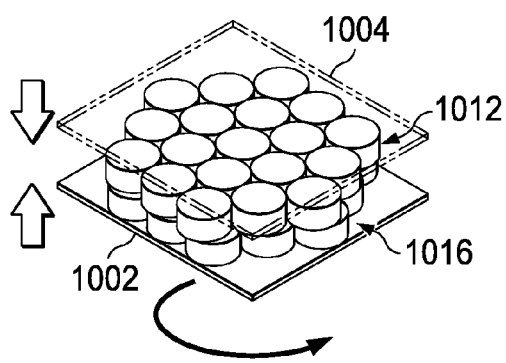
Figure 11E:
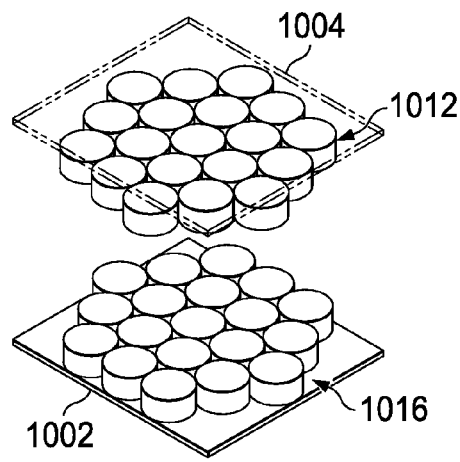
Figure 11C:
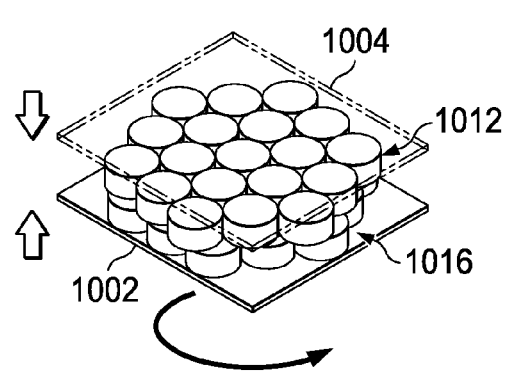
Figure 11F:
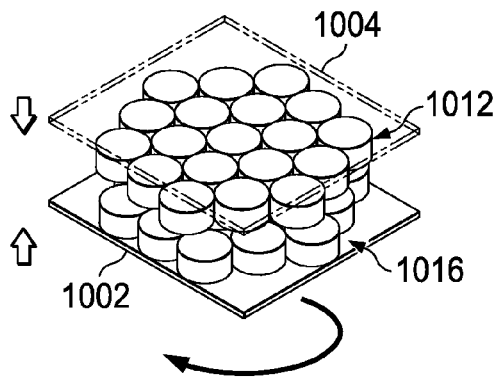
Figure 11G:
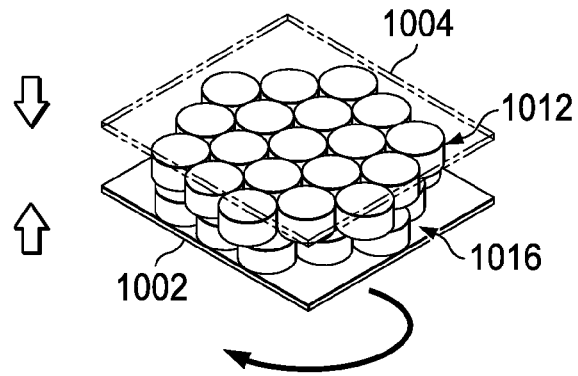
Figure 11H:
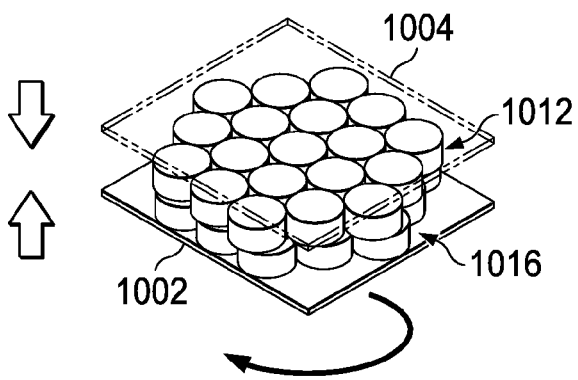
Figure 11I:
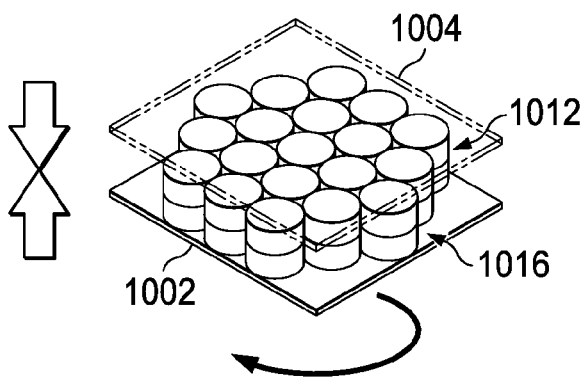

Referring to FIGS. 11A-11I, there is depicted an exemplary selected first magnetic field emission structure 1012 (associated with the interface 1004) and its mirror image second magnetic field emission structure 1016 (associated with the artificial prosthesis 1002) and the resulting spatial forces produced in accordance with their various alignments as they are twisted relative to each other which enables one to attach or remove the artificial prosthesis 1002 to or from the interface 1004. In FIG. 11A, the first magnetic field emission structure 1012 and the mirror image second magnetic field emission structure 1016 are aligned producing a peak spatial force. In FIG. 11B, the second magnetic field emission structure 1016 is rotated counter-clockwise slightly relative to the mirror image first magnetic field emission structure 1012 and the attractive force reduces significantly. In this example, the person 1008 would physically turn the artificial prosthesis 1002. In FIG. 11C, the second magnetic field emission structure 1016 is further rotated counter-clockwise and the attractive force continue to decrease. In FIG. 11D, the second magnetic field emission structure 1016 is still further rotated counter-clockwise until the attractive force becomes very small, such that the two magnetic field emission structures 1012 and 1016 are easily separated as shown in FIG. 11E. One skilled in the art would also recognize that the artificial prosthesis 1002 can be detached from the interface 1004 by applying a pull force, shear force, or any other force sufficient to overcome the attractive peak spatial force between the substantially aligned first and second field emission structures 1012 and 1016. Given the two magnetic field emission structures 1012 and 1016 are held somewhat apart as in FIG. 11E, the two magnetic field emission structures 1012 and 1016 can be moved closer and rotated towards alignment producing a small spatial force as shown in FIG. 11F. The spatial force increases as the two magnetic field emission structures 1012 and 1016 become more and more aligned in FIGS. 11G and 11H and a peak spatial force is achieved when aligned as in FIG. 11I. It should be noted that the direction of rotation was arbitrarily chosen and may be varied depending on the code employed. Additionally, the first and second magnetic field emission structures 1012 and 1016 are mirror images of one another which results in an attractive peak spatial force (see also FIGS. 3-4). This way of securing and removing the artificial prosthesis 1002 to and from the interface 1004 is a marked-improvement over the prior art in which the conventional prosthetic device employed straps or other mechanical fastening mechanisms which required a great degree of dexterity and strength on the part of the person 1008 to use when they wanted to attach or remove the artificial prosthesis 1002 to or from the interface 1004.

In operation, the person 1008 could place, properly align, and secure the interface 1004 which incorporates the first magnetic field emission structure 1012 onto their residual limb 1006. The person 1008 would then pick-up and move the artificial prosthesis 1004 which incorporates the second magnetic field emission structure 1016 towards the interface 1004. Then, the person 1008 would align the first and second magnetic field emission structures 1012 and 1016 such that the artificial prosthesis 1002 can be attached to the interface 1004 when the first and second magnetic field emission structures 1012 and 1016 are located next to one another and have a certain alignment with respect to one another in which they correlate with each other to produce a peak attractive force. The person 1008 can release the artificial prosthesis 1002 from the interface 1004 by turning the first and second magnetic field emission structures 1012 and 1016 relative to one another so as to misalign the two field emission structures 1012 and 1016. Alternatively, the artificial prosthesis 1002 may incorporate a release mechanism (not shown) that the person 1008 can turn or press to rotate the second field emission structure 1016 with respect to the first field emission structure 1012 so as to attach and detach the artificial prosthesis 1002 to and from the interface 1004.

The process of attaching and detaching the artificial prosthesis 1002 to and from the interface 1004 is possible because each of the first and second magnetic field emission structures 1012 and 1016 includes an array of field emission sources 1012a and 1016a each having positions and polarities relating to a desired spatial force function that corresponds to a relative alignment of the first and second magnetic field emission structures 1012 and 1016 within a field domain. Each field emission source of each array of field emission sources 1012a and 1016a has a corresponding field emission amplitude and vector direction determined in accordance with the desired spatial force function, where a separation distance between the first and second magnetic field emission structures 1012 and 1016 and the relative alignment of the first and second magnetic field emission structures 1012 and 1016 creates a spatial force in accordance with the desired spatial force function. The field domain corresponds to first field emissions from the array of first field emission sources 1012a of the first magnetic field emission structure 1012 interacting with second field emissions from the array of second field emission sources 1016a of the second magnetic field emission structure 1016.

Figure 12A:
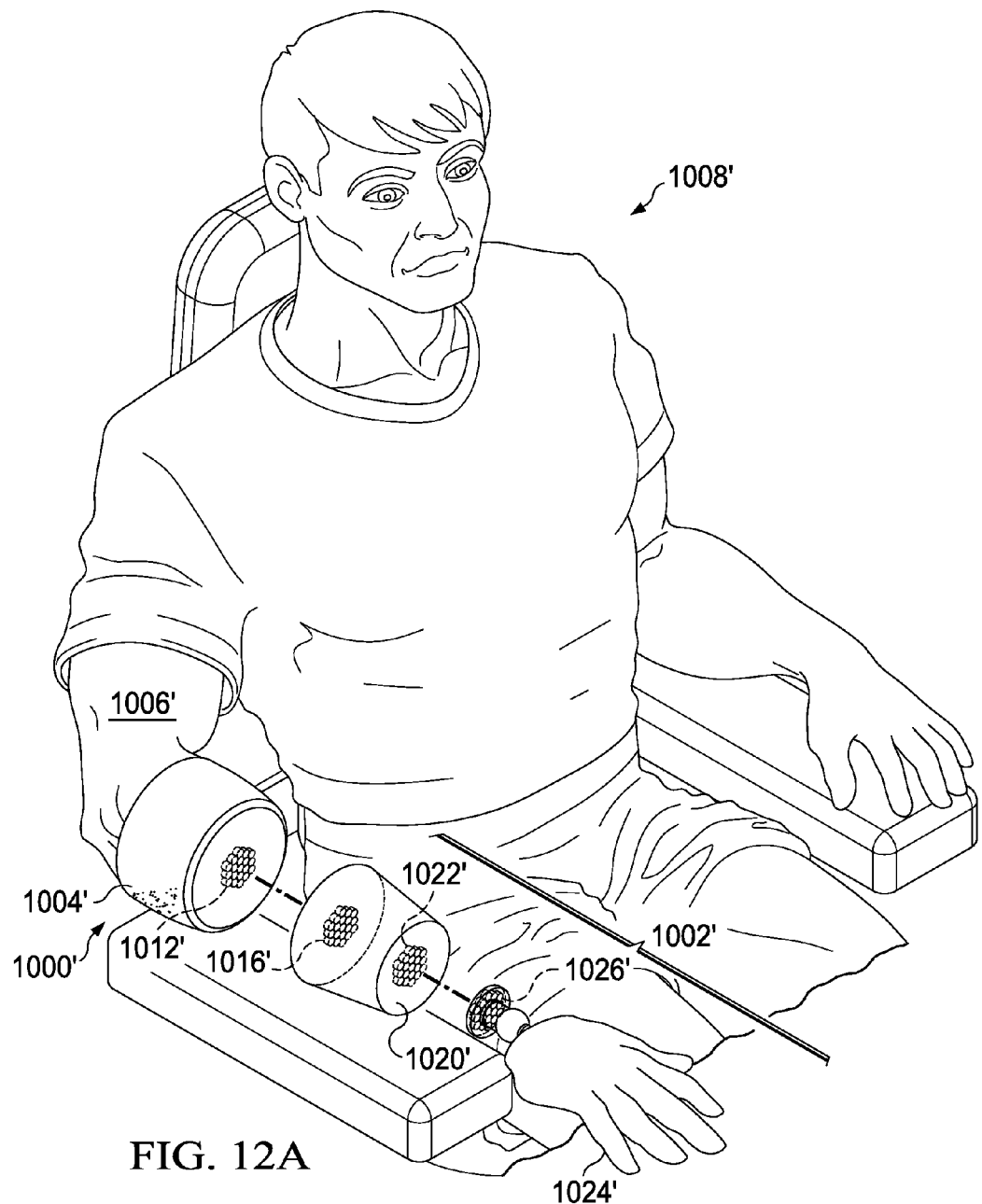
FIGS. 12A-12B are several diagrams of an exemplary correlated magnetic prosthetic device (e.g., artificial arm) in accordance with an embodiment of the present invention.
Figure 12B:
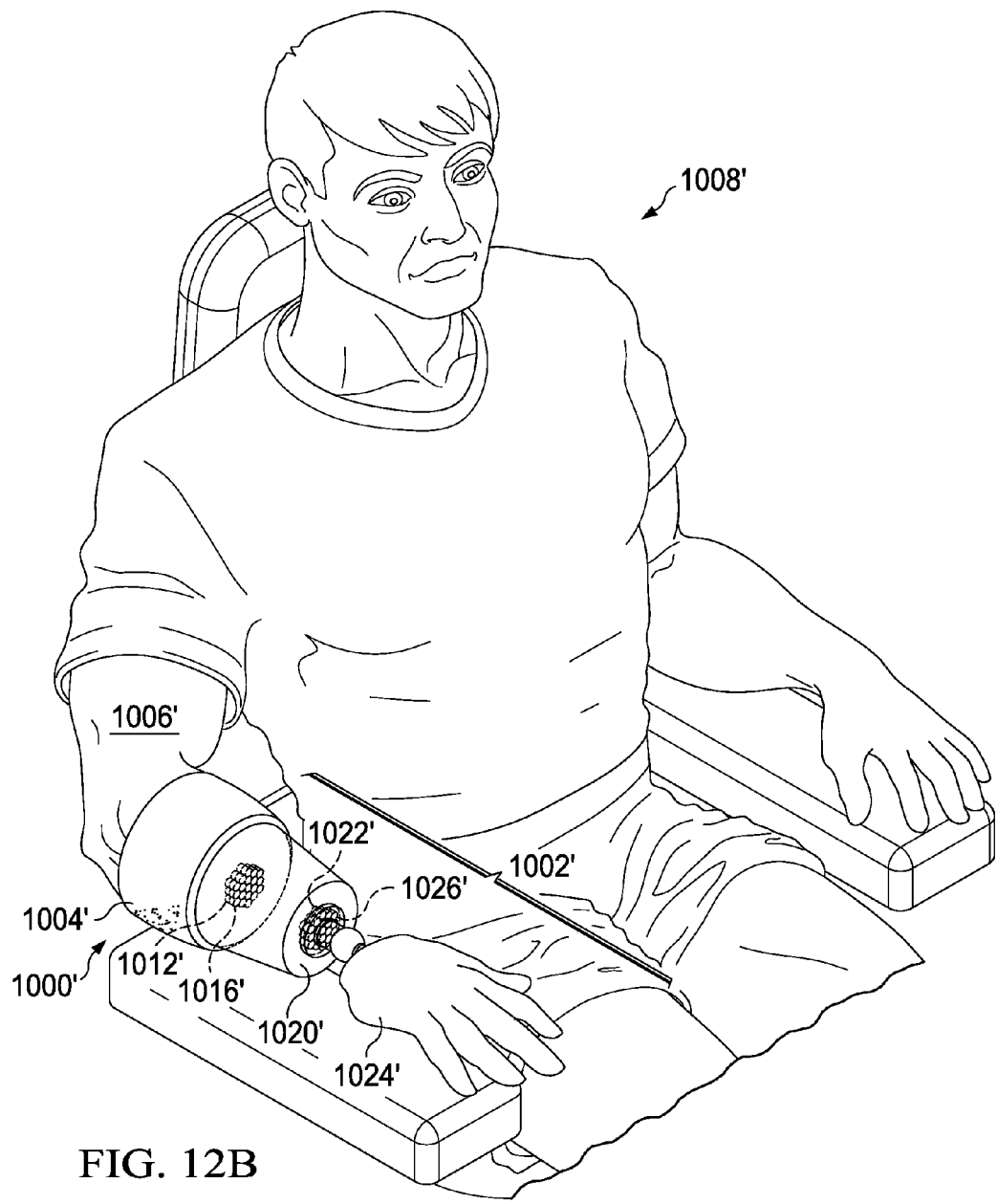

Referring to FIGS. 12A-12B, are several diagrams of an exemplary prosthetic device 1000' that has a correlated magnetic artificial prosthesis 1002' (e.g., artificial arm 1002') that can be easily and effectively attached to and removed from a correlated magnetic interface 1004' (e.g., prosthetic liner 1004') which is secured to a residual limb 1006' of a person 1008' in accordance with an embodiment of the present invention. In this example, the artificial prosthesis 1002' can be attached to the interface 1004' when their respective first and second magnetic field emission structures 1012' and 1016' are located next to one another and have a certain alignment with respect to one another (see FIG. 12B). The artificial prosthesis 1002' can be released from the interface 1004' when their respective first and second magnetic field emission structures 1012' and 1016' are turned relative to one another (see FIG. 12A). Alternatively, the artificial prosthesis 1002' may incorporate a release mechanism (not shown) that the person 1008 can turn or press to rotate the second field emission structure 1016' with respect to the first field emission structure 1012' so as to attach and detach the artificial prosthesis 1002' to and from the interface 1004'. The configuration and operation of the first and second field emission structures 1012' and 1016' are not discussed herein since they are the same as or similar to the first and second field emission structures 1012 and 1016 that have been discussed in detail above with respect to the exemplary prosthetic device 1000.

In this example, the artificial prosthesis 1002' also has an optional coupling device 1020' which includes a third field emission structure 1022' and an optional living aid device 1024' (e.g., hand 1024') which includes a fourth field emission structure 1026'. The third magnetic field emission structure 1022' is configured to interact (correlate) with the fourth magnetic field emission structure 1026' such that the living aid device 1024' can, when desired, be substantially aligned to become attached (secured) to the coupling device 1020' or misaligned to become removed (detached) from the coupling device 1020'. In particular, the living aid device 1024' can be attached to the coupling device 1020' when the third and fourth magnetic field emission structures 1022' and 1026' are located next to one another and have a certain alignment with respect to one another (see FIG. 12B). The living aid device 1024' can be released from the coupling device 1020' when the third and fourth magnetic field emission structures 1022' and 1026' are turned with respect to one another (see FIG. 12A). In this example, the living aid device 1024' is configured to be an artificial hand but it could be any one of a wide variety of devices that can be attached to the end of the artificial prosthesis 1002' such as, for example, a hand tool (e.g., hammer, saw, pipe wrench), a kitchen-cutlery tool (e.g., cheese grater, pizza cutter, whisk), a sporting device (e.g., fishing rod). If desired, the aforementioned artificial leg 1002 may also incorporate a coupling device 1020' and different types of living aid devices 1024'.

Figure 13:
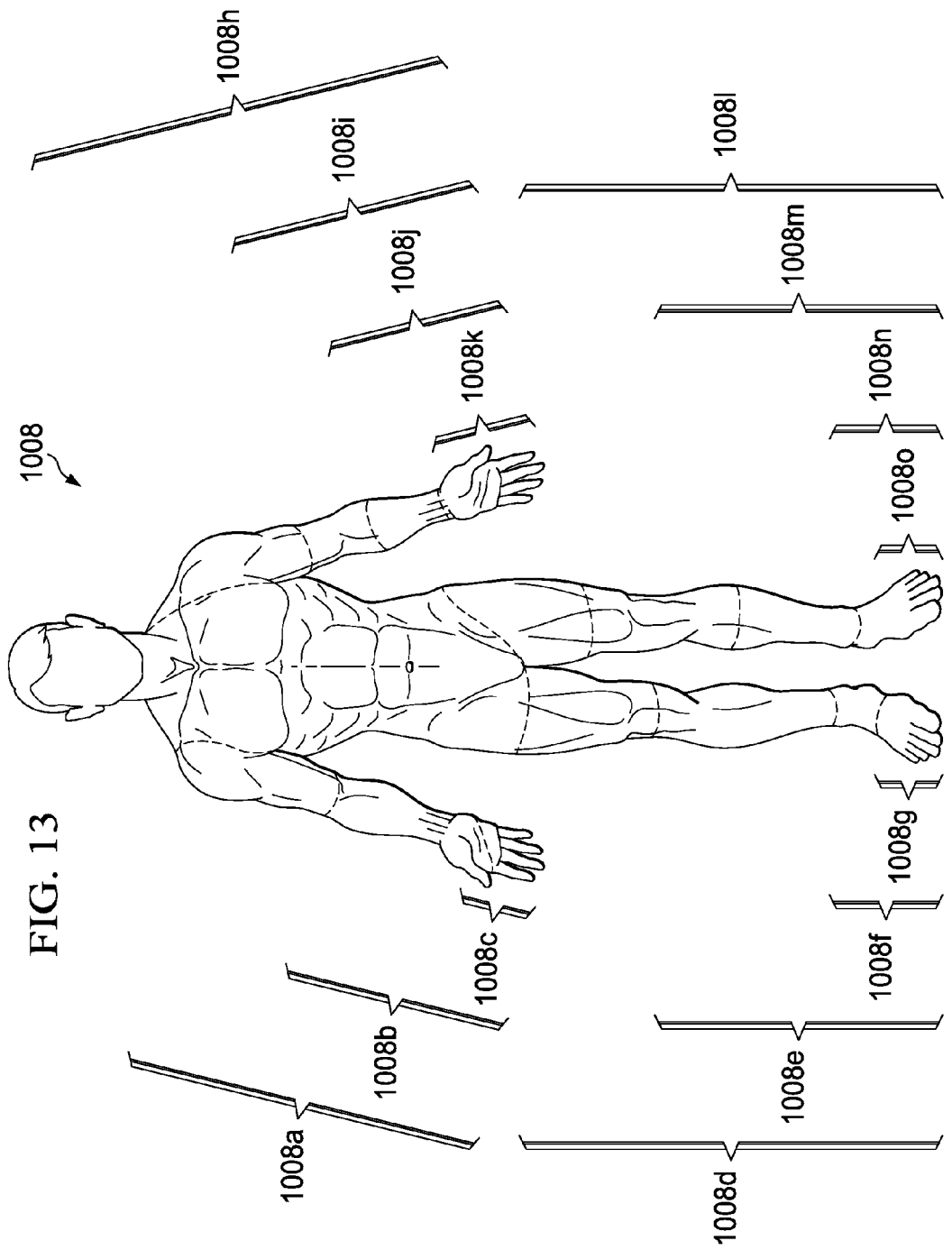
FIG. 13 illustrates a diagram of a person illustrating different types of correlated magnetic prosthetic devices that can be used in accordance with an embodiment of the present invention.

Referring to FIG. 13, there is a diagram of the person 1008 that illustrates several different types of exemplary correlated magnetic prosthetic devices 1000a, 1000b . . . 1000o that can be used in accordance with an embodiment of the present invention. For instance, the person 1008 could have any one of the following types of correlated magnetic prosthetic devices: (1) shoulder disarticulation prosthetic device 1000a; (2) elbow disarticulation prosthetic device 1000b; (3) partial hand prosthetic device 1000c; (4) hip disarticulation prosthetic device 1000d; (5) knee disarticulation prosthetic device 1000e; (6) ankle disarticulation prosthetic device 1000f; (7) partial foot prosthetic device 1000g; (8) forequarter prosthetic device 1000h; (9) above-elbow prosthetic device 1000i; (10) below-elbow prosthetic device 1000j; (11) hand and wrist disarticulation prosthetic device 1000k; (12) hermipelvectomy prosthetic device 1000l; (13) above-knee prosthetic device 1000m; (14) below-knee prosthetic device 1000n; and (15) symes prosthetic device 1000o. The correlated magnetic prosthetic device 1000a, 1000b . . . 1000o can either mechanical, electrical or a hybrid of mechanical-electrical prostheses. The person 1008 could use other types of correlated magnetic prosthetic devices in addition to the aforementioned prosthetic devices 1000, 1000', 1000a, 1000b . . . 1000p such as for example one or more correlated magnetic teeth or correlated magnetic dentures as described below with respect to FIGS. 14A-14B.

Figure 14B:
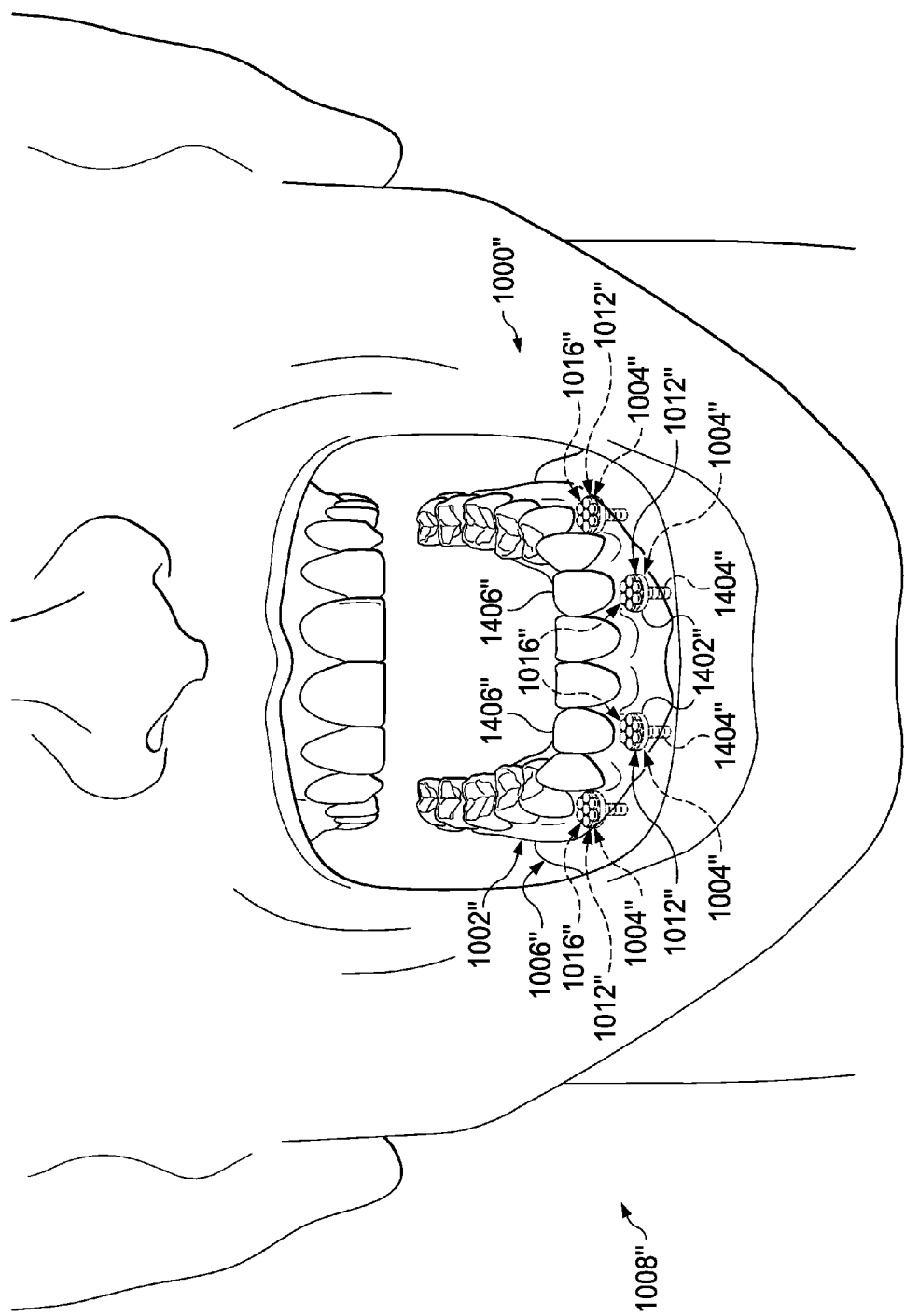

Referring to FIGS. 14A-14B, there are several diagrams of an exemplary prosthetic device 1000" which has a correlated magnetic artificial prosthesis 1002" (e.g., lower denture 1002") that can be easily and effectively attached to and removed from one or more correlated magnetic interfaces 1004" (e.g., keepers 1004") which are secured to a residual limb 1006" (e.g., anterior mandible 1006") of the person 1008". In this example, there are four interfaces 1004" each of which is configured as a keeper that has a top surface 1402" which incorporates a first field emission structure 1012" and a threaded-portion 1404" which would be secured-screwed to the person's residual limb 1006" (anterior mandible 1006"). The artificial prosthesis 1002" is configured as a lower denture that has teeth 1406" and in this case four second field emission structures 1016".

In this arrangement, the artificial prosthesis 1002" can be attached to the interfaces 1004" when their respective first and second magnetic field emission structures 1012" and 1016" are located next to one another and have a certain alignment with respect to one another (see FIG. 14B). The artificial prosthesis 1002" can be released from the interfaces 1004" when their respective first and second magnetic field emission structures 1012" and 1016" are turned with respect to one another (see FIG. 12A). Alternatively, the artificial prosthesis 1002" can be detached from the interfaces 1004 by applying a pull force, shear force, or any other force sufficient to overcome the attractive peak spatial force between the substantially aligned first and second field emission structures 1012" and 1016". The configuration and operation of the first and second field emission structures 1012" and 1016" are not discussed herein since they are the same as or similar to the first and second field emission structures 1012 and 1016 that have been discussed in detail above with respect to the exemplary prosthetic device 1000.

Although multiple embodiments of the present invention have been illustrated in the accompanying Drawings and described in the foregoing Detailed Description, it should be understood that the present invention is not limited to the disclosed embodiments, but is capable of numerous rearrangements, modifications and substitutions without departing from the invention as set forth and defined by the following claims. It should also be noted that the reference to the "present invention" or "invention" used herein relates to exemplary embodiments and not necessarily to every embodiment that is encompassed by the appended claims.

The invention claimed is:

1. A prosthetic device to be used by a person, said prosthetic device comprising:
   an interface including a first field emission structure, where the interface is secured to a residual limb on the person; and
   an artificial prosthesis including a second field emission structure, where the artificial prosthesis is attached to the interface when the first and second field emission structures are located next to one another and have a certain alignment with respect to one another, where each of the first and second field emission structures include field emission sources having positions and polarities relating to a desired spatial force function that corresponds to a relative alignment of the first and second field emission structures within a field domain, said spatial force function being in accordance with a code, said code corresponding to a code modulo of said first plurality of field emission sources and a complementary code modulo of said second plurality of field emission sources, said code defining a peak spatial force corresponding to substantial alignment of said code modulo of said first plurality of field emission sources with said complementary code modulo of said second plurality of field emission sources, said code also defining a plurality of off peak spatial forces corresponding to a plurality of different misalignments of said code modulo of said first plurality of field emission sources and said complementary code modulo of said second plurality of field emission sources, said plurality of off peak spatial forces having a largest off peak spatial force, said largest off peak spatial force being less than half of said peak spatial force.

2. The prosthetic device of claim 1, wherein the artificial prosthesis is released from the interface when the first and second field emission structures are turned with respect to one another so the person is able to remove the artificial prosthesis.

3. The prosthetic device of claim 1, further includes a release mechanism which is used to turn the first and second field emission structures relative to one another to release the artificial prosthesis from the interface so the person is able to remove the artificial prosthesis.

4. The prosthetic device of claim 1, wherein the artificial prosthesis further includes:
   a coupling device including a third field emission structure; and
   a living aid device including a fourth field emission structure, where the living aid device is attached to the coupling device when the third and fourth field emission structures are located next to one another and have a certain alignment with respect to one another, where each of the third and fourth field emission structures include field emission sources having positions and polarities relating to another desired spatial force function that corresponds to a relative alignment of the third and fourth field emission structures within another field domain.

5. The prosthetic device of claim 1, wherein the interface is one or more keepers that are attached to the residual limb on the person.

6. The prosthetic device of claim 1, wherein the interface is a prosthetic liner that covers at least a portion of the residual limb on the person.

7. The prosthetic device of claim 1, wherein the artificial prosthesis includes an artificial foot, an artificial leg, an artificial hand, an artificial arm, an artificial tooth, or an artificial denture.

8. The prosthetic device of claim 1, wherein said positions and said polarities of each of said field emission sources are determined in accordance with at least one correlation function.

9. The prosthetic device of claim 8, wherein said at least one correlation function is in accordance with at least one code.

10. The prosthetic device of claim 9, wherein said at least one code is at least one of a pseudorandom code, a deterministic code, or a designed code.

11. The prosthetic device of claim 9, wherein said at least one code is one of a one dimensional code, a two dimensional code, a three dimensional code, or a four dimensional code.

12. The prosthetic device of claim 1, wherein each of said field emission sources has a corresponding field emission amplitude and vector direction determined in accordance with the desired spatial force function, wherein a separation distance between the first and second field emission structures and the relative alignment of the first and second field emission structures creates a spatial force in accordance with the desired spatial force function.

13. The prosthetic device of claim 12, wherein said spatial force include at least one of an attractive spatial force or a repellant spatial force.

14. The prosthetic device of claim 12, wherein said spatial force corresponds to a peak spatial force of said desired spatial force function when said first and second field emission structures are substantially aligned such that each field emission source of said first field emission structure substantially aligns with a corresponding field emission source of said second field emission structure.

15. The prosthetic device of claim 1, wherein said field domain corresponds to first field emissions from said field emission sources of said first field emission structure interacting with second field emissions from said second field emission sources of said second field emission structure.

16. The prosthetic device of claim 1, wherein said polarities of the field emission sources include at least one of North-South polarities or positive-negative polarities.

17. The prosthetic device of claim 1, wherein at least one of said field emission sources includes a magnetic field emission source or an electric field emission source.

18. The prosthetic device of claim 1, wherein at least one of said field emission sources include a permanent magnet, an electromagnet, an electret, a magnetized ferromagnetic material, a portion of a magnetized ferromagnetic material, a soft magnetic material, or a superconductive magnetic material.

19. A method for enabling a person to attach and remove an artificial prosthesis to and from an interface that is secured to a residual limb on the person, said method comprising the steps of:
securing the interface which includes a first field emission structure to the residual limb;
moving the artificial prosthesis which includes a second field emission structure towards the interface; and
aligning the first and second field emission structures so the artificial prosthesis attaches to the interface when the first and second field emission structures are located next to one another and have a certain alignment with respect to one another, where each of the first and second field emission structures include field emission sources having positions and polarities relating to a desired spatial force function that corresponds to a relative alignment of the first and second field emission structures within a field domain, said spatial force function being in accordance with a code, said code corresponding to a code modulo of said first plurality of field emission sources and a complementary code modulo of said second plurality of field emission sources, said code defining a peak spatial force corresponding to substantial alignment of said code modulo of said first plurality of field emission sources with said complementary code modulo of said second plurality of field emission sources, said code also defining a plurality of off peak spatial forces corresponding to a plurality of different misalignments of said code modulo of said first plurality of field emission sources and said complementary code modulo of said second plurality of field emission sources, said plurality of off peak spatial forces having a largest off peak spatial force, said largest off peak spatial force being less than half of said peak spatial force.

20. The method of claim 19, further comprising a step of turning the first and second emission structures relative to another so the person is able to remove the artificial prosthesis.

21. The method of claim 19, wherein the artificial prosthesis further includes:
a coupling device including a third field emission structure; and
a living aid device including a fourth field emission structure, where the living aid device is attached to the coupling device when the third and fourth field emission structures are located next to one another and have a certain alignment with respect to one another, where each of the third and fourth field emission structures include field emission sources having positions and polarities relating to another desired spatial force function that corresponds to a relative alignment of the third and fourth field emission structures within another field domain.

* * * * *